(12) United States Patent
Gandrud et al.

(10) Patent No.: US 11,195,403 B2
(45) Date of Patent: Dec. 7, 2021

(54) ACTIVITY-BASED RULES FOR COMPLIANCE DETECTION USING BODY-WORN OFFENDER MONITORING ELECTRONIC DEVICES

(71) Applicant: ATTENTI ELECTRONIC MONITORING LTD., Tel Aviv (IL)

(72) Inventors: Jonathan Dale Gandrud, Woodbury, MN (US); Arash Sangari, St. Paul, MN (US); David Solomon Segal, Palm Harbor, FL (US); Nicholas Andrew Asendorf, St. Paul, MN (US); Saber Taghvaeeyan, St. Paul, MN (US)

(73) Assignee: ATTENTI ELECTRONIC MONITORING LTD, Tel Aviv (IL)

( * ) Notice: Subject to any disclaimer, the term of this patent is extended or adjusted under 35 U.S.C. 154(b) by 0 days.

(21) Appl. No.: 16/622,933

(22) PCT Filed: Jun. 14, 2018

(86) PCT No.: PCT/IL2018/050662
§ 371 (c)(1),
(2) Date: Dec. 16, 2019

(87) PCT Pub. No.: WO2018/229777
PCT Pub. Date: Dec. 20, 2018

(65) Prior Publication Data
US 2021/0150870 A1 May 20, 2021

Related U.S. Application Data

(60) Provisional application No. 62/520,615, filed on Jun. 16, 2017, provisional application No. 62/534,490, filed on Jul. 19, 2017.

(51) Int. Cl.
*H04W 4/02* (2018.01)
*G08B 21/02* (2006.01)
(Continued)

(52) U.S. Cl.
CPC ......... *G08B 21/0269* (2013.01); *G01C 17/02* (2013.01); *G01C 19/00* (2013.01);
(Continued)

(58) Field of Classification Search
CPC ........ H04W 4/029; H04W 4/02; H04W 64/00
See application file for complete search history.

(56) References Cited

U.S. PATENT DOCUMENTS

| 2013/0076523 A1 | 3/2013 | Kwan et al. | |
| 2016/0110987 A1* | 4/2016 | Hughes | H04W 4/029 340/573.4 |
| 2016/0354014 A1* | 12/2016 | Lobner | A61B 5/0004 |

\* cited by examiner

*Primary Examiner* — Benyam Haile
(74) *Attorney, Agent, or Firm* — Soroker Agmon Nordman

(57) ABSTRACT

A system for tracking a location of a body-worn tracking device (BWTD) includes a global navigation satellite system (GNSS) component, one or more sensors, one or more processors, and a memory device. The memory device includes instructions that, when executed by the one or more processors, cause the one or more processors to determine whether a current location of the BWTD can be determined using the GNSS component. The instructions also cause the one or more processors to determine, based in part on the activity of the wearer of the BWTD and based on a determination that the current location of the BWTD cannot be determined using the GNSS component, whether to perform an action. The instructions also cause the one or more processors to perform the action in response to a determination to perform the action.

18 Claims, 10 Drawing Sheets

(51) Int. Cl.
    *G01C 17/02*     (2006.01)
    *G01C 19/00*     (2013.01)
    *G01P 15/18*     (2013.01)
    *G01S 19/01*     (2010.01)
    *G16H 40/67*     (2018.01)
    *A61B 5/11*     (2006.01)
    *G06Q 50/26*     (2012.01)

(52) U.S. Cl.
    CPC .............. *G01P 15/18* (2013.01); *G01S 19/01* (2013.01); *H04W 4/02* (2013.01); *A61B 5/1112* (2013.01); *G06Q 50/26* (2013.01); *G16H 40/67* (2018.01)

ACTIVITY-BASED RULES FOR COMPLIANCE DETECTION USING BODY-WORN OFFENDER MONITORING ELECTRONIC DEVICES

This application is related to U.S. Provisional Patent Application 62/520,615 filed Jun. 16, 2017 and to U.S. Provisional Patent Application 62/534,490 filed Jul. 19, 2017, the entire content of both is incorporated by reference.

TECHNICAL FIELD

This disclosure relates to information systems for tracking geospatial location information related to monitored persons or objects.

BACKGROUND

Released criminal offenders on community supervision, either probation or parole, may be monitored with body-worn tracking devices (BWTDs) by a criminal justice supervising agency, such as a department of corrections or local law enforcement. The monitoring is based on a sentence, and often includes restricted regions and permissible regions with a schedule for the day of the week and a range of times associated with those areas when the released criminal offender is required to be or required not to be in those areas1. A released criminal offender's geospatial location at a given date and time is monitored and recorded by tracking devices worn or carried by the released criminal offender. This geospatial information, including date and time information, can be used to determine a released criminal offender's compliance with their sentence. Activities of released criminal offenders can be reported to the criminal justice supervising agency or to a probation or parole officer by fax, page, text message or email generated by a monitoring center unique to the criminal justice supervising agency.

SUMMARY

Techniques of this disclosure are directed to detecting compliance with geographic boundaries using a body-worn tracking devices (BWTD) worn by a monitored person. In some examples, a computing device (e.g., a processor of a BWTD, a local computer, a server of a monitoring system, etc.) determines whether the BWTD is within a bounded geographic region when the BWTD is unable to determine its current location by using a Global Navigation Satellite System (GNSS). For example, the BWTD may lose connectivity to one or more GNSS satellites (e.g., Global Positioning System (GPS) satellites) when the monitored person wearing the BWTD enters his or her place of employment. As described herein, the computing device may be configured to determine a current activity of the monitored person and, responsive to the determined activity, dynamically adapt a grace period for requiring re-establishment of GNSS connectivity.

For example, for activities that may result in a high level of travel during loss of GNSS connectivity, such as a determination that the user is biking, driving or running, the computing device may decrease the configured grace period. For activities that may result in a reduced level of travel during loss of GNSS connectivity, such as a determination that the user is sleeping or walking, the computing device may increase the configured grace period, thereby avoiding technical burdens on the network and computing resources.

As a result, rather than outputting a notification at a fixed time when the BWTD loses a GNSS signal, the computing device may more efficiently output notifications as a function of the current activity being performed during the time period when GNSS signal loss occurs, which may advantageously reduce the burden on computing resources of the BWTD and/or a receiving monitoring system, the amount of data transferred between the BWTD and monitoring system, and generally the number of notifications processed and provided to the monitored person and/or law enforcement. Reducing the number of notifications may improve processing efficiencies, and ease the burden on monitored persons and/or law enforcement in assisting monitored persons to stay within permitted geographic boundaries.

In an example, this disclosure describes a system for tracking a location of a body-worn tracking device (BWTD), the system comprising: a global navigation satellite system (GNSS) component; one or more sensors; a set of one or more processors; and one or more memory devices comprises instructions that, when executed by the one or more processors, cause the one or more processors to: determine that a current location of the BWTD cannot be determined using the GNSS component; determine, based on data generated by the one or more sensors, an activity of a wearer of the BWTD, the activity of the wearer being a form of locomotion or a sedentary activity; and responsive to determining the activity of the wearer of the BWTD and a determination that the current location of the BWTD cannot be determined using the GNSS component, performing an action.

In another example, this disclosure describes a method comprising: determining, by a set of processors in a system for tracking a location of a body-worn tracking device (BWTD), that a current location of the BWTD cannot be determined using a global navigation satellite system (GNSS) component of the system, the set of processors including one or more processors; determining, by the one or more processors, based on data generated by one or more sensors, an activity of a wearer of the BWTD, the activity of the wearer being a form of locomotion or a sedentary activity; and performing, by the one or more processors, an action based in part on the activity of the wearer of the BWTD and based on a determination that the current location of the BWTD cannot be determined using the GNSS component.

In another example, this disclosure describes a system comprising means for performing this method. In another example, this disclosure describes a non-transitory computer-readable medium having instructions stored thereon that, when executed, cause one or more processors to perform this method.

In another example, this disclosure describes a BWTD comprising: a GNSS component; one or more sensors; a set of one or more processors; and one or more memory devices comprising instructions that, when executed by the one or more processors, cause the one or more processors to: determine whether a current location of the BWTD can be determined using the GNSS component; determine, based on data generated by the one or more sensors, an activity of a wearer of the BWTD, the activity of the wearer being a form of locomotion or a sedentary activity; responsive to a determination that the current location of the BWTD cannot be determined using the GNSS component, adjust, based on the activity of the wearer of the BWTD, a duration of a grace period; and generate a notification in response to determining the grace period has expired.

3

The details of one or more examples are set forth in the accompanying drawings and the description below. Other features, objects, and advantages of the disclosure will be apparent from the description, drawings, and claims.

DETAILED DESCRIPTION

Figure 1:
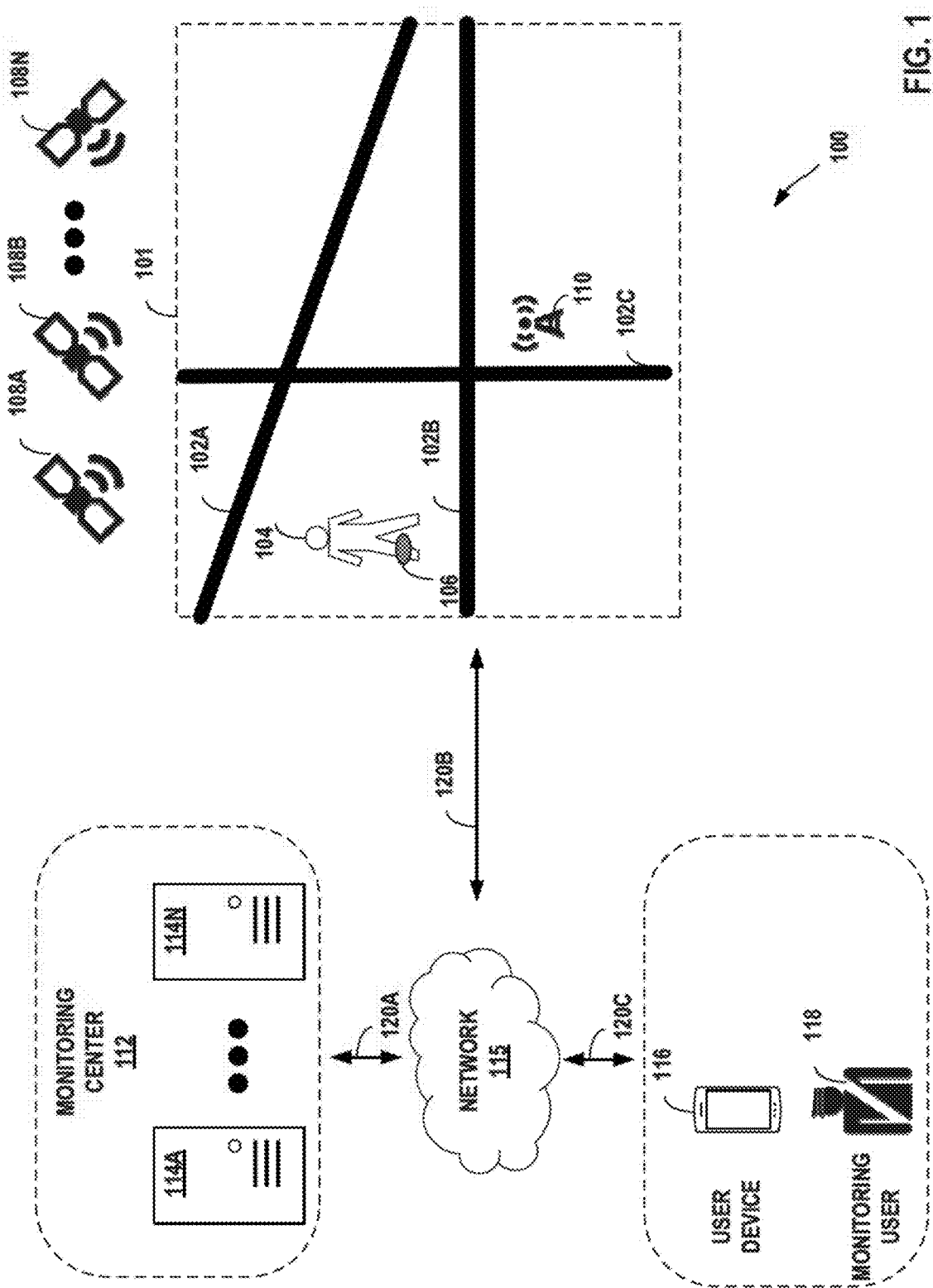
FIG. 1 is a conceptual diagram illustrating an example monitoring system for determining a location of a body-worn tracking device, in accordance with one or more aspects of this disclosure.

In an offender monitoring system, each offender is typically assigned a device (e.g., a body-worn tracking device (BWTD)) that determines and stores a variety of data such as location, speed, heading, or the like at prescribed intervals (e.g., every minute). The device typically includes a Global Navigation Satellite System (GNSS) device (e.g., a Global Positioning System (GPS) receiver) to help determine when the offender violates the terms of his or her parole (e.g., by entering prohibited geographic areas or exiting permitted areas). However, GNSS devices may temporarily lose connectivity to one or more GNSS satellites, for example, due to surrounding structure or environmental features. Losing connectivity to one or more satellites may prevent the BWTD from determining current GNSS coordinates of the BWTD, which may limit the ability of law enforcement to ensure the offender complies with the terms of his or her parole.

Conventionally, when a BWTD is unable to determine the BWTD's current location using a GNSS device, the BWTD starts a grace period. If the grace period expires prior to the BWTD again being able to determine the BWTD's current location using the GNSS device, the BWTD may output a message notifying the offender that he or she is required to re-establish GNSS connectivity. Thus, in one example, when a parolee loses GPS for more than N minutes, the parolee is required to establish a GPS signal or be in violation of parole. This is quite an obnoxious practice if one's work or home does not have a strong GPS signal. In addition, a monitoring system may generate an alert indicating that a wearer of the BWTD is potentially at an unauthorized location. Conventionally, the grace period has a fixed duration. However, the use of a fixed-duration grace period may present several challenges in a monitoring system. For example, if a wearer of a BWTD lives or works in a location where the BWTD frequently loses GNSS connectivity, the wearer may frequently need to go to a location where the BWTD is able to regain GNSS connectivity, no matter what the wearer is doing. This may be extremely disruptive to the life of the wearer and may increase the number of times the monitoring system generates alerts, despite the wearer being at an authorized location. The generation of such necessary alerts may increase the costs to an organization that uses the monitoring system because the organization may need to send out personnel to investigate the alerts.

Thus, there may be a need for greater flexibility in responding to the loss of GNSS connectivity. In accordance with various techniques of this disclosure, instead of using a fixed grace period when a BWTD loses GNSS connectivity, a monitoring system may determine a current activity of a wearer of the BWTD. Additionally, the monitoring system may determine, based in part on the activity of the wearer of the BWTD and based on a determination that the current location of the BWTD cannot be determined using the GNSS component, whether to perform an action. The monitoring system may perform the action in response to a determination to perform the action. As one example, the monitoring system may adaptively modify (i.e., shorten or extend) the grace period at which time an alert is output instructing the offender that the offender is required to re-establish GNSS connectivity. More generally, as one example, an action may comprise configuring the BWTD with a particular grace period that is based at least in part on the determined activity of the wearer. For instance, in this example, there may be predefined grace periods for different activities.

In some examples, to determine whether to perform the action, the monitoring system may evaluate a set of rules. The rules may include activity-dependent rules. Each respective activity-dependent rule in the set of activity-dependent rules specifies a condition that is satisfied if the wearer of the BWTD performs a particular activity of a plurality of activities and if the current location of the BWTD is not determinable using the GNSS component. The monitoring system makes the determination to perform the action in response to determining the condition is satisfied. Furthermore, in some examples, the conditions specified by the activity-dependent rules may be satisfied if the BWTD does not regain GNSS connectivity within grace periods of different durations. For instance, there may be a longer grace period for sleeping than for running. The use of different rules for different activities may reduce the frequency with which the monitoring system generates alerts despite wearers of BWTDs being at authorized locations.

FIG. 1 is a conceptual view illustrating an example monitoring system 100 for determining a location of a body-worn tracking device, in accordance with one or more aspects of this disclosure. Monitoring system 100 comprises a body-worn tracking device (BWTD) 106, satellites 108A through 108N (collectively, "satellites 108"), a monitoring center 112, a network 115, a user device 116. People shown in the example of FIG. 1 are not considered part of monitoring system 100. A monitored target 104 wears BWTD 106. Monitoring system 100 tracks the location of BWTD 106, and thereby tracks the location of monitored target 104. Although not shown in the example of FIG. 1 for the sake of simplicity, monitoring system 100 may track the locations of multiple BWTDs, and thereby track the locations of multiple monitored targets.

In the example of FIG. 1, monitored target 104 and BWTD 106 are located within a geographic region 101, which may be a portion of the Earth's surface. In this example, geographic region 101 includes multiple roads 102A-102C ("roads 102") on which monitored target 104 may travel. Geographic region 101 may include human built structures (e.g., houses, buildings, and the like) and/or natural structures (trees, mountains, oceans, lakes, and the like).

In the example of FIG. 1, monitored target 104 is a person wearing BWTD 106. However, in other examples, a monitored target may be a non-human object to which a BWTD is attached. For instance, a monitored target may be a vehicle, animal, or any other movable object that may move to different locations in a geographic area. In examples where a monitored target is non-human, a BWTD may be any device that is attached to, accompanies or is otherwise physically associated with the movable object, even if not necessarily bodily worn.

Monitored target 104 may be a released criminal offender, although in other examples a monitored target may be any person. Released criminal offenders may be criminal offenders who have been suspected, accused, or convicted of a crime and released from a jail or prison. For instance, when monitored target 104 is released from jail, prison, or other facility, BWTD 106 may be attached by law enforcement to the body of monitored target 104. In some examples, monitored target 104 is an individual with certain a psychological condition, such as dementia or Alzheimer's disease, that makes the individual likely to leave safe areas. In such examples, a caregiver may use BWTD 106 to monitor the location of such an individual.

BWTD 106 may comprise a portable computing device that determines its current location and reports the determined location to monitoring center 112 or another physically separate computing device. Furthermore, BWTD 106 may include a physical housing constructed of plastic or any other suitable material. The housing may include electronics such as, but not limited to: one or more computer processors, one or more memories, one or more wired and/or wireless communication devices (e.g., cellular network component, WiFi component, short-range (e.g., a Near Field Communication (NFC) component, a Bluetooth component, a Universal Serial Bus (USB) component), one or more output devices (e.g., a haptic feedback component, one or more lights, one or more user interface display components, one or more audio components), one or more GNSS components (e.g., a GPS receiver), one or more sensor components (e.g., an accelerometer, a gyroscope, a magnetometer, etc.), one or more power sources (e.g., battery, power supply), and one or more circuit boards that physically, communicatively, and/or electronically couple such components to one another within the housing of BWTD 106.

Each respective satellite of satellites 108 transmits a respective satellite signal indicating a current time and a current location of the respective satellite. GNSS components of BWTD 106 may include a combination of software and hardware components to receive the satellite signals transmitted by satellites 108. In some examples, satellites 108 are global navigation satellites in a global navigation satellite system (GNSS). Example global navigation satellite systems include the GPS satellite network, the Galileo satellite network, the GLONASS satellite network, and other government- or commercially-operated satellite networks. Each satellite signal received by the GNSS components of BWTD 106 from a satellite of satellites 108 includes data such as the current position of the particular satellite and the current time. Although the example of FIG. 1 only shows three satellites, different numbers of satellites may be used by BWTD 106 to determine the GNSS coordinates of BWTD 106 at a point in time.

In some examples, BWTD 106 is a one-piece design in which GNSS hardware and all other hardware for the BWTD are included in a single physical housing. In other examples, BWTD 106 may not include GNSS hardware, which may be physically separate from, but in communication with, BWTD 106. For instance, monitored target 104 may carry a physical device with GNSS hardware (e.g., such as a telephone having GNSS functionality), and separately BWTD 106 may be attached to monitored target 104 and in communication with the GNSS hardware. Further details of the components included within BWTD 106 are illustrated and described in FIGS. 2 and 3.

In some examples, BWTD 106 may further include a combination of software components and hardware components to perform one or more monitoring functions. For instance, BWTD 106 may include a location detection component comprised of hardware and/or software that communicates with the GNSS hardware component to determine and record GNSS coordinates of BWTD 106. For example, location detection components may receive the data from satellites 108 (e.g., data indicative of the position of a particular satellite) via the GNSS components and may determine GNSS coordinates of BWTD 106 based on the data received from satellites 108. In some examples, the location detection component sends such GNSS coordinates of BWTD 106 to monitoring center 112 or other physically separate computing device.

BWTD 106 may have a unique device identifier that is different from unique identifiers of each other BWTD in a set of BWTDs. A database may associate the unique device identifiers with personally identifying information of a monitored target. In this way, as monitored target 104 moves to different locations in a geographic region, geographic location points generated by BWTD 106 and stored at monitoring center 112 may be associated with or otherwise attributed to monitored target 104, such that the location and/or whereabouts of monitored target 104 may be monitored.

Monitoring system 100 may also include one or more towers, such as tower 110, that form cellular network infrastructure. Tower 110 may include a physical structure that supports antennae, a GNSS receiver, one or more sets of digital signal processors, transceivers, and control electronics, which collectively operate to establish sessions with end-user devices such as BWTDs, smartphones, or any other computing device. Tower 110, together with one or more other towers that include similar functionality, may be geographically dispersed, so as to provide a geographically dispersed wireless network for voice and/or data communication. Tower 110 and switching infrastructure (not shown) may be owned and operated by wireless or cellular carrier providers that charge customer/subscriber fees to operate on the wireless or cellular carrier provider.

Figure 4:
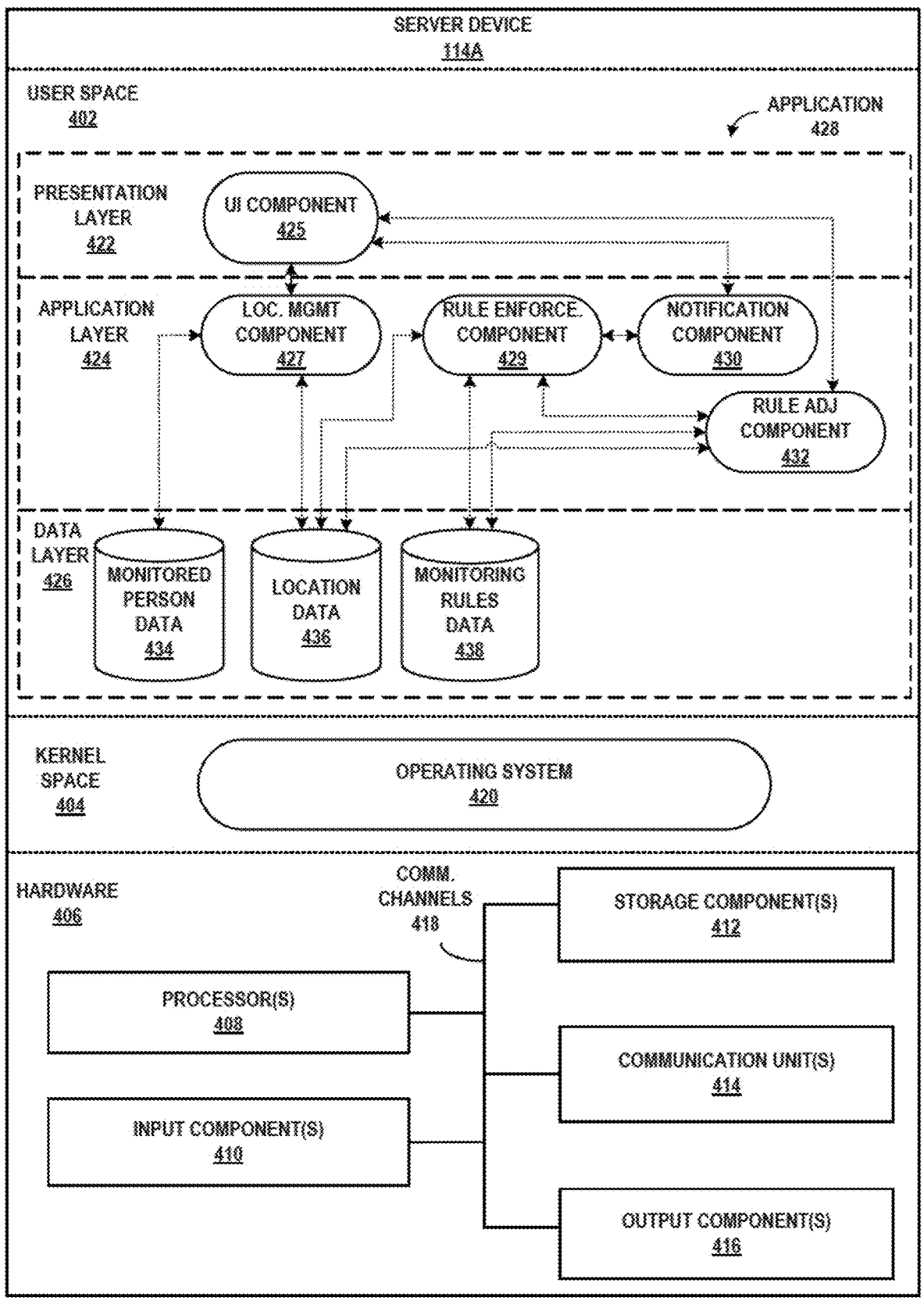
FIG. 4 is a block diagram illustrating example components of server device 114A, in accordance with one or more aspects of the present disclosure.

Monitoring center 112 may be owned and operated by a private entity or a government entity. Monitoring center 112 includes one or more computing devices, such as server devices 114A-114N ("server devices 114"). Further details of the components included within server devices 114 is illustrated in FIG. 4. Server devices 114 may collectively provide a data center to monitor and track monitored persons based on, among other data, GNSS coordinates of BWTDs that are provided to server devices 114.

In some examples, server devices 114 stores an association between a monitored person and a respective BWTD worn by a monitored target. For instance, at the time that a BWTD is attached to the monitored target, a user may use a separate, end-user computing device in communication with monitoring center 112 to provide user input that creates an association between a unique identifier of the monitored target and a unique identifier of the BWTD. For instance, the association may be stored as a record in a database. As GNSS coordinates are received by monitoring center 112 from the BWTD with the unique identifier of the BWTD, monitoring center 112 may store such GNSS coordinates in association with the unique identifier of the BWTD. In this way, an operator of monitoring center 112 may determine the GNSS coordinates associated with a particular monitored person.

Monitoring center 112 may receive configuration input from users, such as law enforcement officers, that specify condition-action rules. A condition-action rule may specify one or more actions monitoring system 100 performs in response to the condition specified by the condition-action rule being satisfied. For example, a condition-action rule may specify an action to be performed if BWTD 106 moves into an unauthorized area. Such configuration input may be sent by a computing device of the user to monitoring center 112 via network 115. The configuration input may specify a unique identifier of the monitored person and/or BWTD and may also include properties such as named locations, perimeters, GNSS coordinates or any other properties that may be used to define authorized and/or unauthorized areas. By associating authorized and/or unauthorized areas with a BWTD and/or monitored target wearing the BWTD, monitoring center 112 can determine violations, such as, determining whether a monitored person is operating within a restricted area and/or exits a permitted area.

In some examples, an action of a condition-action requires monitoring center 112 to send one or more notifications. In some examples, monitoring center 112 may send a notification via network 115 to BWTD 106 for the violation, which may cause BWTD 106 to output an alert (e.g., haptic, visual, and/or audio feedback). In some examples, as part of performing an action specified by a condition-action rule, monitoring center 112 may send notifications to one or more other users, who may be associated with the monitored person who is in violation. For instance, to determine the one or more other users associated with the monitored target, monitoring center 112 may store within a record of a database a unique identifier of a law enforcement officer in association with a unique identifier of a monitored person.

Monitoring center 112 may generate user interfaces for display, such as maps that indicate different locations at which a monitored offender has been physically present. In some examples, monitoring center 112 may illustrate different locations at which a monitored offender has been physically present over a period of time. Monitoring center 112 may output any data that in any suitable format including still and moving image data, audio data, and the like. For instance, geographic region 101 may be visually represented in a map, which may be two- or three-dimensional. Such maps may be output for display by computing devices as further described in this disclosure. In the example of FIG. 1, a map generated based on geographic region 101 may be visually similar in appearance to the representation of geographic region 101 as illustrated in FIG. 1.

In the example of FIG. 1, a monitoring user 118 uses user device 116. Although FIG. 1 shows user device 116 as a smartphone, user device 116 may be various types of computing device. For example, user device 116 may be a laptop computer, a tablet computer, a smartphone, a desktop computer, a server computer, a body worn computer (e.g., smartwatch, head-mounted device), or any other suitable computing device. Although the example of FIG. 1 shows monitoring system 100 as only including a single user device 116, monitoring system 100 may comprise multiple user devices performing functions similar to user device 116.

User device 116 may include one or more components comprising a combination of hardware and software. For instance, user device 116 may execute a monitoring application implemented in software and executable on hardware of user device 116. The monitoring application may provide notifications of violations, maps or other visual representations of monitored offender locations based on real-time or past-generated GNSS coordinates. The monitoring application may also generate and send data that associates a unique identifier of a BWTD with a unique identifier of a monitored person. In some examples, the monitoring application may natively implement functionality described in this disclosure, while in other examples the monitoring application may be a web-browser that accesses a web-based application with such functionality via a web-hosted application executing at monitoring center 112.

Monitoring user 118 may be a law enforcement officer, parole officer, or another type of public safety official or employee. In some examples, monitoring user 118 is a non-public safety office/employee, such as past or potential victims of a monitored offender, a school administrator, or another type of user that may be interested in or need to know of the location or violations of a monitored target. User device 116 may provide notifications to monitoring user 118 in response to messages sent by monitoring center 112.

Network 115 may represent a publicly accessible computer network that is owned and operated by a service provider, which is usually large telecommunications entity or corporation. Although not illustrated in the example of FIG. 1, network 115 may be coupled to one or more networks administered by other providers, and may thus form part of a large-scale public network infrastructure, e.g., the Internet. Network 115 may provide computing devices, such as BWTD 106, user device 116, and monitoring center 112, with access to the Internet, and may allow the computing devices to communicate with each other. In some examples, network 115 may include one or more local area networks (LANs), such that user device 116 may communicate with monitoring center 112 through the Internet and/or a LAN on which both monitoring center 112 and user device 116 are included.

Although additional network devices are not shown in the example of FIG. 1 for ease of explanation, it should be understood that network 115 and monitoring system 100 may comprise additional network and/or computing devices such as, for example, one or more additional switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. It should be understood that one or more additional network elements may be included along any of network links 120A-120C, such that the devices of monitoring system 100 are not directly coupled. Network links 120A-120C may be wired or wireless communication links, such as 100 Mbps, 1 Gbps, or 10 Gbps WiFi connections and/or physical cable connections, to name only a few examples.

To monitor a location of monitored target 104, BWTD 106 may be attached to monitored target 104. In some examples, BWTD 106 includes a tamper-resistant strap that binds BWTD 106 to monitored target 104. BWTD 106 may include one or more components comprised of hardware and/or software that detect if monitored target 104 or another person have tampered with the tamper-resistant strap and/or the housing/internal components of BWTD 106. If BWTD 106 detects that a tampering event is occurring or has occurred, BWTD 106 may send a message via network 115 to monitoring center 112 to indicate the tampering event.

User device 116 may receive indications of user input from monitoring user 118 that define an association between BWTD 106 and monitored target 104 in monitoring center 112. In other words, monitored target 104 may be assigned to wear BWTD 106. User device 116, for example, may output a graphical user interface for display. The graphical user interface may include one or more user interface components, such as input fields, dropdown menus, labels or text fields, or any other graphical component through which BWTD 106 may receive indications of user input from monitoring user 118.

In the example of FIG. 1, user device 116 may receive indications of user input from monitoring user 118 that specify or select a unique identifier of BWTD 106 and may further receive one or more user inputs from monitoring user 118 that specify or select a unique identifier of monitored target 104. In addition to receiving an indication of user input specifying or selecting the unique identifiers of BWTD 106 and/or monitored target 104, user device 116 may receive input from monitoring user 118 to define an association between the respective unique identifiers. User device 116 may send one or more messages to monitoring center 112 that define the association between the unique identifier of monitored target 104 and BWTD 106.

In some examples, user device 116 may receive indications of user input defining condition-action rules. For example, user device 116 may receive an indication of user input defining a condition-action rules that specifies an action to be performed in response to BWTD 106 entering an unauthorized area or leaving an authorized area. In another example, user device 116 may receive indications of user inputs from monitoring user 118 defining a condition-action rule in which an action is to be performed in response to BWTD 106 exceeding permissible times or distances that monitored target 104 is allowed to travel or otherwise move about. User device 116 may send one or more messages to monitoring center 112 with the condition-action rules specified by monitoring user 118, and monitoring center 112 may configure or associate the condition-action rules with the unique identifier of monitored target 104 and BWTD 106.

After BWTD 106 has been attached to monitored target 104, monitored target 104 may be released from custody (i.e., released from a confined or restricted condition, such as a jail, prison, or courthouse). As monitored target 104 moves throughout a geographic region, such as geographic region 101, BWTD 106 determines respective GNSS locations of BWTD 106 and sends messages to monitoring center 112 that may include at least a unique identifier of BWTD 106 and/or monitored target 104, unique tower identifier, GNSS coordinates (latitude, longitude), and timestamps for when each respective GNSS coordinate has been determined. BWTD 106 may send such messages through wireless communication with tower 110, which in turns sends the messages to monitoring center 112 via network 115, and in some examples one or more additional, intermediate networked devices (not shown in FIG. 1).

BWTD 106 includes one or more sensor components comprised of hardware and/or software that detects movement of BWTD 106. In some examples, the one or more sensor components include a plurality of sensing components, such as an accelerometer, one or more directionality sensors (e.g., a gyroscope, a magnetometer, and/or other sensors for determining a spatial orientation), and so on. BWTD 106 may receive acceleration data from the accelerometer that indicates amounts of acceleration various axes, such as a vertical axis and a horizontal axis. BWTD 106 may determine a change in the orientation (e.g., direction) of BWTD 106 for each step based on orientation data received from the directionality sensor (e.g., the gyroscope and/or the magnetometer). BWTD 106 may determine the direction of BWTD 106 relative to Earth's magnetic field based on data received from the magnetometer. In some examples, BWTD 106 sends raw data (e.g., acceleration over time) or processed data (e.g., number of steps, length and direction of each step, or net distance) to monitoring center 112 or other physically separate computing device.

As noted above, existing monitoring technology depends on GNSS data to observe the location, movement, and behavior of monitoring targets. However, GNSS is not available in all areas, such as indoor spaces or in the shadows of tall buildings. Thus, there may be times when BWTD 106 is unable to determine its current location using the GNSS. In other words, there may be times when BWTD 106 lose GNSS connectivity. When BWTD 106 loses GNSS connectivity, BWTD 106 may output an indication that monitored target 104 must move to a GNSS-accessible location. In this disclosure, a GNSS-accessible location is a location at which BWTD 106 can determine a current location of BWTD 106 using the GNSS. BWTD 106 gives monitored target 104 a particular amount of time to move to a GNSS-accessible location. This amount of time is referred to as a "grace period." For example, BWTD 106 may give monitored target 104 ten minutes to reach a GNSS-accessible location. Conventionally, the grace period is a fixed amount of time. If BWTD 106 is unable to determine its current location using the GNSS by the time the grace period expires, user device 116 may alert monitoring user 118 that monitored target 104 is potentially at an unauthorized location.

There are circumstances where BWTD 106 is at an authorized location, but BWTD 106 is unable to determine its current location using the GNSS. For example, if monitored target 104 sleeps or works in a basement area of a building, BWTD 106 may lose GNSS connectivity. In this example, the sleep or work of monitored target 104 may be frequently interrupted by the need to go to a GNSS-accessible location. Going to a GNSS-accessible location can be extremely disruptive to monitored target 104, potentially forcing monitored target 104 to change homes or jobs. Moreover, the need for monitored target 104 to frequently go to a GNSS-accessible location may increase the chances that monitored target 104 is unable to reach a GNSS-accessible location, despite monitored target 104 being at an authorized location. As a result, monitoring system 100 may alert monitoring user 118 unnecessarily. Responding to such unnecessary alerts may increase the costs of operating and using monitoring system 100.

Techniques of this disclosure may improve monitoring system 100 by potentially reducing the number of unnecessary alerts generated by monitoring system 100. Reducing the number of alerts may reduce the frequency of data transfers and amount of data transferred between the BWTD and the monitoring center, which may increase battery life of the BWTD and may decrease network traffic. Reducing the number of alerts may also reduce the time and resources consumed by law enforcement administrators in supervising monitored persons. Reducing the number of alerts may ease the burden on monitored persons by reducing how often the BWTD needs to reacquire a GNSS signal.

As noted above, monitoring system 100 may be configured with one or more condition-action rules that specify actions to perform in response to specified conditions being satisfied. Monitoring system 100 may evaluate the condition-action rules to determine whether to perform actions, such as generating alerts to monitoring user 118.

In accordance with one or more techniques of this disclosure, the condition-action rules may include one or more activity-dependent rules. Activity-dependent rules correspond to various activities performed by a wearer of BWTD 106. Such activities may include various forms of locomotion, such as walking, running, driving or riding in or on a motor vehicle, bicycling, swimming, skating, skateboarding, and so on, and various forms of sedentary activities, such as sleeping or staying relatively still. In general, an activity may correspond to an identifiable output signature of one or more sensors. In other words, a signature may correspond to a pattern of output signals or data generated by one or more sensors and each different activity may have a different signature. In general, an activity-dependent rule for a particular activity is a condition-action rule that specifies, as a condition, that a wearer of BWTD 106 is performing the particular activity. Accordingly, to evaluate the activity-based rules, monitoring system 100 (e.g., monitoring center 112 and/or BWTD 106) determines, based on data from one or more sensors, a current activity of a wearer of BWTD 106 (i.e., a current activity of monitored target 104).

Monitoring system 100 may perform various actions in response to determining the conditions specified by an activity-dependent rule is satisfied. For example, monitoring system 100 generate an alert in response to determining that the conditions specified by the activity-dependent rule are satisfied. For instance, following the expiration of a grace period whose duration has been dynamically adjusted based on the activity of the wearer of BWTD 106, BWTD 106 may generate an alert indicating that the wearer must move to a location within GNSS connectivity to avoid being in violation of parole. Thus, rather than generating such an alert in response to determining that a fixed grace period has expired, monitoring system 100 may generate an alert in response to determining that the conditions specified by an activity-dependent rule have been satisfied.

Activity-dependent rules for different activities may specify different conditions. For instance, in some examples, activity-dependent rules for different activities have conditions involving different activities. In some examples, activity-dependent rules for different activities may specify actions performed if BWTD 106 does not regain GNSS connectivity prior to expirations of grace periods of various durations. For example, an activity-dependent rule for sleeping may specify an action performed if BWTD 106 does not regain GNSS connectivity prior to the expiration of an 8-hour grace period. Thus, in this example, if BWTD 106 is unable to regain GNSS connectivity and monitored target 104 is sleeping, monitoring system 100 does not generate an alert until 8 hours have passed. In this example, monitoring system 100 may consider monitored target 104 to be in violation of this activity-dependent rule if BWTD 106 does not regain GNSS connectivity prior to the expiration of the 8-hour grace period. However, in this example, an activity-dependent rule for walking may specify an action performed if BWTD 106 does not regain GNSS connectivity prior to the expiration of a 20-minute grace period. In this example, an activity-dependent rule for running may specify an action performed if BWTD 106 does not regain GNSS connectivity prior to the expiration of a 5-minute grace period. In other words, BWTD 106 and/or monitoring system 112 may dynamically adapt the grace period for requiring GNSS connectivity as a function of a determined activity being performed by the user. For activities that may result in a high level of travel during loss of GNSS connectivity, such as a determination that the user is biking, driving or running, BWTD 106 and/or monitoring system 112 may decrease the configured grace period. For activities that may result in a reduced level of travel during loss of GNSS connectivity, such as a determination that the user is sleeping or walking, BWTD 106 and/or monitoring system 112 may increase the configured grace period, thereby avoiding technical burdens on the network and computing resources.

Thus, in more general terms, the set of activity-dependent rules may include at least a first rule and a second rule. Satisfaction of the first vile may require the wearer of the BWTD to perform a first activity, the BWTD to have lost GNSS connectivity, and a first grace period to have expired prior to the BWTD regaining GNSS connectivity. Satisfaction of the second rule may require the wearer of the BWTD to perform a second activity, the BWTD to have lost GNSS connectivity, and a second grace period to have expired prior to the BWTD regaining GNSS connectivity. In this example, the first activity is different from the second activity and the first grace period and the second grace period have different durations.

In this way, the activity-dependent rules may be used to adjust the duration of the grace period based on the activities of monitored target 104. Thus, through the use of such activity-dependent rules, if monitoring system 100 determines that monitored target 104 has remained stationary when BWTD 106 lost GNSS connectivity, monitoring system 100 may use an extended grace period. However, if monitoring system 100 detects that monitored target 104 is driving or running, monitoring system 100 may use a shortened grace period. More broadly, through the use of the activity-dependent rules, monitoring system 100 may adaptively set the grace period depending on an activity of monitored target 104. For instance, monitoring system 100 may adaptively set the grace period such that activities deemed harmless may extend the grace period while activities deemed potentially dangerous may reduce the grace period.

Although each of the example activity-dependent rules above specify conditions involving expirations of grace periods, other activity-dependent rules may specify conditions that do not involve grace periods. For example, an activity-dependent rule for walking may specify an action performed if a net displacement of BWTD 106 from a location at which BWTD 106 most recently had GNSS connectivity is greater than a distance threshold. In this example, monitoring system 100 may be able to determine the net displacement of BWTD 106 based on data generated by sensors included in BWTD 106.

Thus, in a more general example, monitoring system 100 may determine a distance traveled. In this example, the distance traveled is a net distance traveled by the BWTD from a location at which the one or more processors were most recently able to determine the current location of the BWTD using the GNSS component. In this example, the set of activity-dependent rules includes a first rule and a second rule. Satisfaction of the first rule may require the wearer of the BWTD to perform a first activity, the BWTD to have lost GNSS connectivity, and the distance traveled to be greater than a first threshold. Satisfaction of the second rule may require the wearer of the BWTD to perform a second activity, the BWTD to have lost GNSS connectivity, and the distance traveled to be greater than a second threshold. In this example, the first activity is different from the second activity and the first threshold is different from the second threshold. In some examples, the one or more sensors include an accelerometer, a gyroscope, and/or a magnetometer. As part of determining the net distance, monitoring system 100 may detect or count, based on data generated by an accelerometer, a plurality of steps. Additionally, monitoring system 100 may determine an estimated distance traveled during each step of the plurality of steps. Monitoring system 100 may also determine (e.g., based on the data generated by one or more directionality sensors, such as the gyroscope and/or the magnetometer), a direction of travel of each step of the plurality of steps. Monitoring system 100 may determine, based on the estimated distance traveled during each step and the direction of travel of each step, the net distance between the current location of the BWTD and the location at which the one or more processors were most recently able to determine the current location of the BWTD using the GNSS component.

A condition specified by an activity-dependent rule include sub-conditions in addition to the wearer performing a particular activity and BWTD 106 having lost GNSS connectivity. For example, an activity-dependent rule may specify an action to be performed if monitored target 104 is performing activity X, BWTD 106 has lost GNSS connectivity, and BWTD 106 has not regained GNSS connectivity prior to an expiration of a 10-minute grace period or BWTD 106 has a net displacement of more than fifty meters from a location at which BWTD 106 was most recently had GNSS connectivity. For instance, by using accelerometer and magnetometer data, monitoring system 100 can determine the net distance travelled by an offender by counting the number of steps the offenders has taken in certain directions. The associated compliance calculation (e.g., condition evaluation) for the walking activity then can compare the net distance travelled to a pre-defined threshold which allows for a maximum distance travelled. Under the walking activity, if the offender has not moved a large net distance, then monitoring system 100 adaptively adjusts the grace period to give the offender a longer period of time to re-establish GNSS.

Other conditions specified by condition-action rules may depend on still other types of data. For example, a condition may depend on a sound environment, a battery life of BWTD 106, whether other monitored targets are within particular distance thresholds, whether detected accelerations of BWTD 106 are able particular thresholds, and so on.

Figure 2:
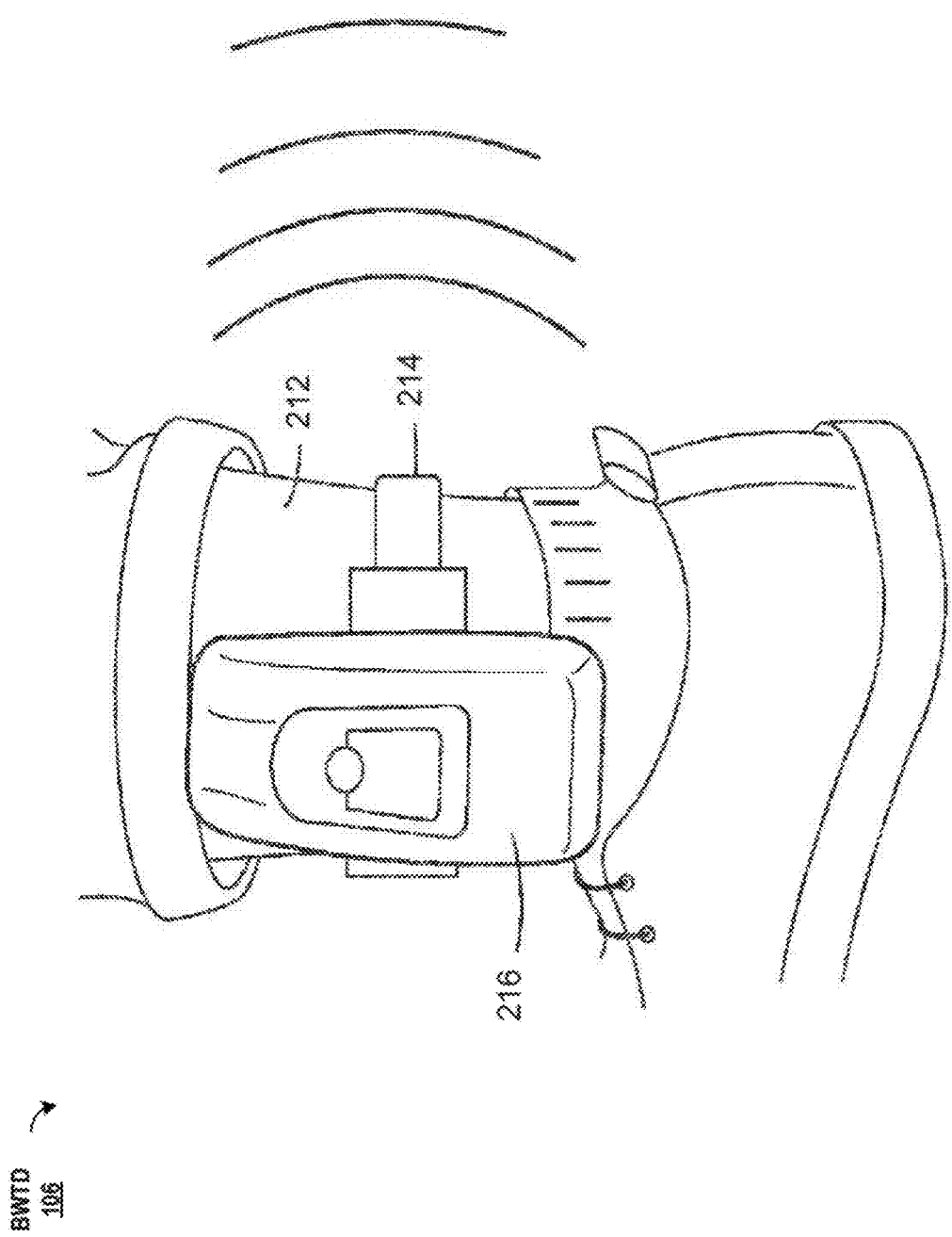
FIG. 2 is a perspective view of an example body-worn tracking device, in accordance with one or more aspects of the present disclosure.

FIG. 2 is a perspective view of an example BWTD, in accordance with one or more aspects of the present disclosure. BWTD 106 may be configured to implement various aspects of this disclosure. FIG. 2 illustrates only one particular example of BWTD 106, as shown in FIG. 1. Many other examples of BWTD 106 may be used in other instances. Other BWTDs may include different subsets of the components than those of the example of BWTD 106 shown in FIG. 2. As illustrated in FIG. 2, BWTD 106 may be attached to an ankle 212 of monitored target 104. Furthermore, as illustrated in FIG. 2, BWTD 106 includes a strap 214 and a housing 216. Housing 216 includes or contains a variety of components such as one or more processors configured to perform the techniques described herein, one or more storage components for storing instructions executable by the processor along with data, one or more GNSS components, one or more sensors, and one or more communication units. The one or more communication units may enable BWTD 106 to communicate wirelessly with an external device.

Figure 3:
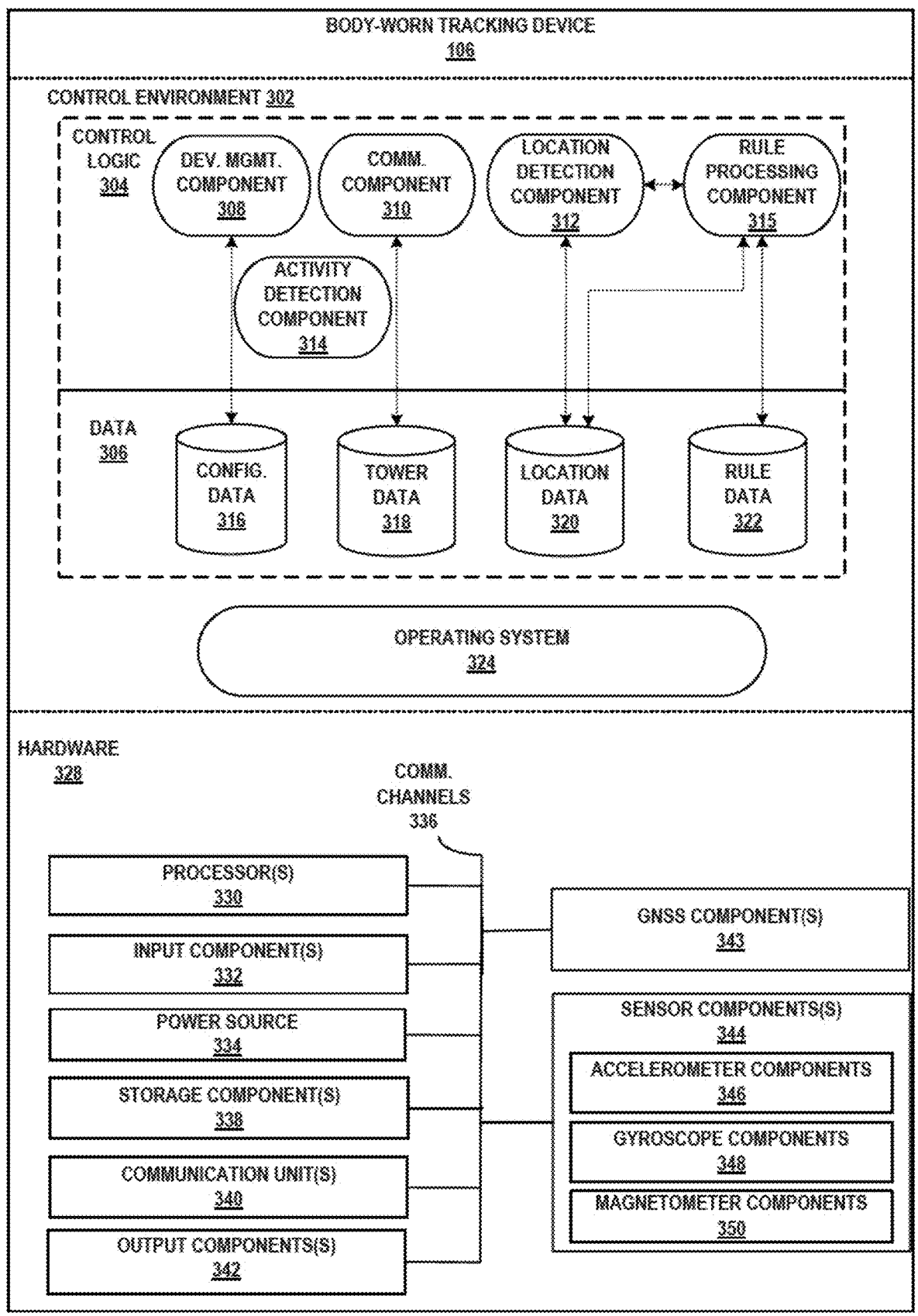
FIG. 3 is a block diagram illustrating example components of a body-worn tracking device, in accordance with one or more aspects of the present disclosure.

FIG. 3 is a block diagram illustrating example components of BWTD 106, in accordance with one or more aspects of the present disclosure. FIG. 3 illustrates only one particular example of BWTD 106, as shown in FIG. 1 or FIG. 2. Many other examples of BWTD 106 may be used in other instances and may include a subset of the components included in example BWTD 106 or may include additional components not shown in FIG. 3. In some examples, BWTD 106 may run a set, subset, or superset of functionality included in control logic 304. In some examples, the external housing (not shown) of BWTD 106 may have one or more attachment components (not shown), such as straps, fasteners, magnetic materials, adhesive materials or any other mechanism or material for attaching or associating with tracking device 106A with an object to be tracked.

As shown in the example of FIG. 3, BWTD 106 may be logically divided into control environment 302 and hardware 328. Hardware 328 may include one or more hardware components that provide an operating environment for components executing in control environment 302. Control environment 302 may include operating system 324, which or may not operate with higher privileges than other components executing in control environment 302.

As shown in FIG. 3, hardware 328 includes one or more processors 330, input components 332, power source 334, storage components 338, communication units 340, output components 342, GNSS components 343, and sensor components 344. Processors 330, input components 332, power source 334, storage components 338, communication units 340, output components 342, GNSS components 343, and sensor components 344 may each be interconnected by one or more communication channels 336. Communication channels 336 may interconnect each of the components 330, 332, 334, 338, 340, 342, 343, and 344 for inter-component communications (physically, communicatively, and/or operatively). In some examples, communication channels 336 may include a hardware bus, a network connection, one or more inter-process communication data structures, or any other components for communicating data between hardware and/or software.

One or more processors 330 may implement functionality and/or execute instructions within BWTD 106. For example, processors 330 on BWTD 106 may receive and execute instructions stored by storage components 338 that provide the functionality of components included in control environment 302. These instructions executed by processors 330 may cause BWTD 106 to store and/or modify information, within storage components 338 during program execution. Processors 330 may execute instructions of components in control environment 302 to perform one or more operations in accordance with techniques of this disclosure. That is, components included in user control environment 302 may be operable by processors 330 to perform various functions described herein.

One or more input components 332 of BWTD 106 may receive input. Examples of input are tactile, audio, kinetic, and optical input, to name only a few examples. Input components 332 of BWTD 106, in one example, include a voice responsive system, video camera, buttons, control pad, microphone or any other type of device for detecting input from a human or machine. In some examples, input component 332 may be a presence-sensitive input component, which may include a presence-sensitive screen, touch-sensitive screen, etc.

As shown in FIG. 3, BWTD 106 may include a power source 334. In some examples, power source 334 is a battery. Power source 334 provides power to one or more components of BWTD 106. Examples of power source 334 include, but are not necessarily limited to, batteries having zinc-carbon, lead-acid, nickel cadmium (NiCd), nickel metal hydride (NiMH), lithium ion (Li-ion), and/or lithium ion polymer (Li-ion polymer) chemistries. In some examples, power source 334 may have a limited capacity (e.g., 1000-3000 mAh).

One or more storage components 338 within BWTD 106 may store information for processing during operation of BWTD 106. In some examples, storage components 338 include a temporary memory, meaning that a primary purpose of storage components 338 is not long-term storage. Storage components 338 on BWTD 106 may configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage components 338, in some examples, also include one or more computer-readable storage media. Storage components 338 may be configured to store larger amounts of information than volatile memory. Storage components 338 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage components 338 may store program instructions and/or data associated with components included in control environment 302.

One or more output components 342 of BWTD 106 generate output. Examples of output are tactile output (e.g., haptic output, vibratory output), audio output, and video output. Output components 342 of BWTD 106, in some examples, include a display screen, a presence-sensitive screen, a sound card, a video graphics adapter card, a speaker, a liquid crystal display (LCD), or another type of device for generating output to a human or machine. In some examples, output components 342 are integrated with BWTD 106 and physically connected to the external packaging of BWTD 106. In other examples, output components 342 are physically external to and separate from BWTD 106, but are operably coupled to BWTD 106 via wired or wireless communication.

One or more communication units 340 of BWTD 106 communicate with external devices by transmitting and/or receiving data. For example, BWTD 106 may use communication units 340 to transmit and/or receive radio signals on a radio network such as a cellular radio network. Examples of communication units 340 include a network interface card (e.g. such as an Ethernet card), an optical transceiver, a radio frequency transceiver, or any other type of device that can send and/or receive information. Other examples of communication units 340 include Bluetooth®, 3G, 4G, and Wi-Fi® radios found in mobile devices as well as Universal Serial Bus (USB) controllers and the like. GNSS components 343 receive satellite signals from satellites in a GNSS (e.g., satellites 108 (FIG. 1)). Location detection component 312 may determine, based on the received satellite signals, coordinates corresponding to a location of BWTD 106 at a particular point in time.

In some examples, sensor components 344 include a plurality of sensing components, such as accelerometer components 346, gyroscope components 348, and magnetometer components 350. Gyroscope components 348 and magnetometer components 350 may be instances of directionality sensors. Accelerometer components 346 may generate data indicative of the acceleration of BWTD 106 in at least one plane. In some examples, accelerometer components 346 include a 3-axis accelerometer that detects acceleration in 3-dimensions and generates data indicative of the acceleration in each of the 3-dimensions. Gyroscope components 348 may generate data indicative of a change in the orientation (e.g., direction) of BWTD 106 in one or more of the 3-dimensions. As illustrated in FIG. 3, sensor components 344 may include magnetometer components 350. Magnetometer components 350 may detect a magnetic field (e.g., Earth's magnetic field) and may generate data indicative of the detected magnetic field. Location detection component 312 may determine the orientation of BWTD 106 relative to the magnetic field based on the data generated by magnetometer components 350.

In the example of FIG. 3, control logic 304 executes in control environment 302. Control logic 304 may include but is not limited to: a device management component (DMC) 308, a communication component 310, a location detection component 312, an activity detection component 314, and a rule processing 315. Data 306 may include one or more data stores. A data store may store data in structured or unstructured form. Example data stores may be any one or more of a relational database management system, online analytical processing database, table, or any other suitable structure for storing data. In the example of FIG. 3, data 306 includes configuration data 316, tower data 318, location data 320, and rule data 322. Storage components 338 may store data 306.

Components such as DMC 308, communication component 310, location detection component 312, activity detection component 314, and rule processing component 315 may perform operations described herein using software, hardware, firmware, or a mixture of both hardware, software, and firmware residing in and executing on BWTD 106. In some examples, processors 330 of BWTD 106 may execute various components when embodied in software to perform the functionality described in this disclosure. Processors 330 may execute any of such components as or within a virtual machine, user space application, operating system or any other operating environment executing on underlying hardware.

Configuration data 316 may include one or more of: a unique identifier of BWTD 106, a unique identifier of the monitored person to which BWTD 106 is assigned, and/or any other properties or parameters that control or change the operation of tracking device 106A. Tower data 318 may include records, tuples or sets, wherein each record, tuple or set specifies one or more of: a unique identifier of a particular tower, a latitude and longitude of BWTD 106 when BWTD 106 detected or initiated a communication session with the particular tower, a signal strength for the tower when BWTD 106 detected or initiated a communication session with the particular tower, a directional heading of BWTD 106 when BWTD 106 detected or initiated a communication session with the particular tower, and/or a timestamp when BWTD 106 detected or initiated a communication session with the particular tower.

Location data 320 may include records, tuples or sets, wherein each record, tuple or set specifies one or more of: a unique identifier of BWTD 106 and/or a monitored person wearing BWTD 106, GNSS coordinates (e.g., latitude, longitude), a timestamp when the GNSS coordinates were determined, GNSS signal strength when the GNSS coordinates were determined, signal strength of a tower when the GNSS coordinates were determined, and/or a directional heading of BWTD 106 when the GNSS coordinates were determined.

Rule data 322 may include a set of condition-action rules. If a condition of a condition-action rule is satisfied, monitoring system 100 may perform the action of the condition-action rule. For example, if GNSS coordinates generated by GNSS components 343 indicate that BWTD 106 is in an unauthorized area, monitoring system 100 may generate an alert notifying monitoring user 118. In some examples where the same action is always performed if the conditions of a condition-action rule are satisfied, an action of the condition-action rule may be implicitly defined. For instance, if the action is always generating an alert, it may only be necessary for conditions of rules to be explicitly defined.

Furthermore, in accordance with one or more aspects of this disclosure, the set of condition-action rules include one or more activity-dependent rules. For each respective activity-dependent rule, a condition of the activity-dependent rule specifies that a wearer of BWTD 106 is performing a particular activity. This disclosure describes an activity-dependent rule as corresponding to an activity if the activity-dependent rule has a condition specifying that a wearer of BWTD 106 is performing a particular activity.

In operation, DMC 308 may initially be configured with configuration data 316. For instance, DMC 308 may be programmed, from an external computing device, with a unique identifier for BWTD 106 and/or a unique identifier of the monitored person associated with or assigned to BWTD 106. Once BWTD 106 has been configured with configuration data 316, the monitored person may move about one or more geographic regions. Additionally, DMC 308 may write data to storage components 338 that is received from monitoring center 112 or other computing devices. Data may include restricted regions and/or restricted locations, configuration data to configure one or more components of BWTD 106, information that uniquely identifies BWTD 106 and/or monitored target 104 that is wearing BWTD 106, or any other suitable information.

Communication component 310 may initiate, manage, and terminate communication sessions with towers that provide cellular network infrastructure. In particular, as BWTD 106 moves to different geographic regions, communication component 310 may initiate communication sessions with different towers in the different regions, where a tower may be a Base Station Transceiver in a wireless communication network, such as a cellular network. In this way, communication component 310 maintains communication between BWTD 106 and monitoring center 112. Examples of such cellular networks may include a set of one or more geographically dispersed towers with radios, antennas and/or other communications components that provide for data communication with BWTD 106 using one or more protocols such as 2G, 3G, 4G, Long-Term Evolution (LTE), or any other suitable protocol. Cellular network infrastructure may provide a wireless network for data communication to and from BWTD 106 over a geographically distributed area. In some examples, cellular network infrastructure may be owned and operated by a third-party, wireless or cellular carrier provider.

Location detection component 312 may determine the location (e.g., GNSS coordinates) of BWTD 106 based on data received from GNSS components 343. For instance, GNSS components 343 may receive GNSS signals from a plurality of GNSS satellites (e.g., satellites 108 in FIG. 1). The GNSS signals received from each GNSS satellite may include data indicating a position of a respective GNSS satellite and a time at which the respective GNSS satellite sent the GNSS signal. Location detection component 312 may determine the latitude and longitude of BWTD 106 at a particular point time based on the data received from the GNSS satellites. Location detection component 312 may determine the latitude and longitude on a periodic basis according to an interval that may be included in configuration data 316. The time interval may be programmed by a user, dynamically changed (e.g., based on one or more detected or determined events) or hard-coded. At a point in time (e.g., when a time interval has elapsed), upon determining the latitude and longitude, location detection component 312 may generate and store a record, tuple or set that specifies one or more of: a unique identifier of BWTD 106 and/or monitored person wearing BWTD 106, GNSS coordinates (latitude, longitude), a timestamp when the GNSS coordinates (latitude, longitude) were determined, GNSS signal strength when the GNSS coordinates (latitude, longitude) were determined, signal strength of a tower when the GNSS coordinates (latitude, longitude) were determined, and/or a directional heading of BWTD 106 when the GNSS coordinates (latitude, longitude) were determined. Location detection component 312 may send location data 320 to monitoring center 112 of FIG. 1 in real-time, periodically, or asynchronously.

In some circumstances, location detection component 312 is unable to determine the current location of BWTD 106. For example, GNSS components 343 may be unable to receive GNSS signals from a sufficient number of satellites 108 (FIG. 1) such that location detection component 312 is unable to determine the geospatial location (e.g., GNSS coordinates) of BWTD 106. For instance, GNSS components 343 may be unable to detect GNSS signals from a sufficient number of GNSS satellites when BWTD 106 enters a building or enters a geographical area obstructed by manmade or naturally occurring environmental features.

Activity detection component 314 may determine an activity of a wearer of BWTD 106 (i.e., monitored target 104). In one example, activity detection component 314 uses the data generated by sensor components 344 to determine the activity of monitored target 104. In some examples, the data generated by sensor components 344 is 9-axis data. Activity detection component 314 may use various techniques known in the art to determine an activity of monitored target 104. In other examples, communication component 310 sends data generated by sensor components 344 to a remote device, such as one or more of server devices 114. In this example, one or more processors of the remote device (e.g., processors 408 of FIG. 4) may use the data generated by sensor components 344 to determine the activity of monitored target 104.

Rule processing component 315 may evaluate condition-action rules stored in rule data 322. In accordance with one or more aspects of this disclosure, the condition-action rules evaluated by rule processing component 315 may include activity-dependent rules.

Rule processing component 315 may use various types of data in evaluating condition-action rules. For instance, rule processing component 315 may use location data 320 in evaluating a condition-action rule. Furthermore, in some examples, as part of evaluating a condition-action rule, rule processing component 315 may determine a distance traveled by BWTD 106 since a most recent time location detection component was able to use GNSS components 343 to determine the location of BWTD 106. For instance, a condition-action rule may specify that, if a BWTD 106 has lost GNSS connectivity and a wearer of BWTD 106 is performing a particular activity, and if a net distance traveled is greater than a threshold, monitoring system 100 is to generate an alert. In one example, to determine the net distance traveled, accelerometer components 346 generates acceleration data and rule processing component 315 compares the acceleration data to a template acceleration pattern to detect a plurality of steps or strides. Furthermore, in this example, gyroscope components 348 generate orientation data and rule processing component 315 compares the orientation data to a template orientation pattern to detect a plurality of steps or strides. Rule processing component 315 may more accurately detect steps by comparing the acceleration data and the orientation data to the respective template data patterns. Additionally, rule processing component 315 may determine the distance traveled during each step in the plurality of steps. In some scenarios, rule processing component 315 determines the distance traveled by each step by querying storage components 338 to retrieve a predetermined estimate of a stride length. In some instances, rule processing component 315 determines the distance traveled by each step based on the acceleration data generated by acceleration components 346. For instance, rule processing component 315 may integrate the acceleration data to determine the distance traveled during each step. In some examples, rule processing component 315 determines the direction traveled during each step of the plurality of steps. Rule processing component 315 may determine the direction traveled based on orientation data generated by one or more directionality sensors, such as gyroscope components 348 and/or magnetometer components 350. For instance, rule processing component 315 may integrate the orientation data to determine the change in orientation or direction of BWTD 106 during each step. In some examples, rule processing component 315 calibrates the data generated by gyroscope components 348 using data generated by magnetometer components 350, which may improve the accuracy of the determined direction.

In some examples, rule processing component 315 determines the net distance based on the distance traveled during each step and the direction traveled during each step. For example, each step may be represented by a vector that includes the distance and direction of the respective step. In these examples, rule processing component 315 may sum the vectors to determine the net distance and net direction traveled during the plurality of steps that occurred between the last known location and the current location of BWTD 106.

As part of evaluating some condition-action rules, rule processing component 315 determines whether BWTD 106 is within a bounded area that includes the last known location of BWTD 106. In some examples, rule processing component 315 determines whether BWTD 106 is within the bounded area by determining whether the net distance satisfies the threshold distance. For instance, the bounded area may be represented by a circle and the threshold distance may be the radius of the circle. For example, rule processing component 315 may determine that BWTD 106 is within the bounded area based on determining that the net distance satisfies (e.g., is less than or equal to) the threshold distance. In contrast, rule processing component 315 may determine that BWTD 106 is not within the bounded area if the net distance does not satisfy (e.g., is greater than) the threshold distance.

In some examples, rule processing component 315 determines whether BWTD 106 is within the bounded area based on the net distance and the net direction traveled during the plurality of steps. For example, the bounded area may be represented by a shape other than a circle such that BWTD 106 may travel outside the bounded area if traveling a certain distance in one direction while BWTD 106 may remain within the bounded area if traveling the same distance in a different direction. In some examples, rule processing component 315 may determine the bounded area by querying storage components 338 to determine coordinates defining the bounded area (e.g., 4 coordinate sets may define a rectangular bounded area) and determine whether BWTD 106 remains within the bounded area based on the net displacement and net direction.

In some examples, as part of evaluating a condition-action rule, rule processing component 315 may perform the action specified by the condition-action rule. For example, if a condition-action rule specifies an action that includes generating an alert, rule processing component 315 may use output components 342 to generate the alert. In some examples, rule processing component 315 may use communication units 340 to send data to one or more other devices of monitoring system 100 causing the one or more other devices to perform an action specified by the condition-action rule.

FIG. 4 is a block diagram illustrating example components of server device 114A, in accordance with one or more aspects of the present disclosure. FIG. 4 illustrates only one particular example of server device 114A in monitoring center 112, as shown in FIG. 1. Many other examples of server device 114A may be used in other instances and may include a subset of the components included in example server device 114A or may include additional components not shown in FIG. 4. In some examples, server device 114A may be a server, tablet computing device, smartphone, wrist- or head-worn computing device, laptop, desktop computing device, or any other computing device that may run a set, subset, or superset of functionality included in application 428.

As shown in the example of FIG. 4, server device 114A may be logically divided into user space 402, kernel space 404, and hardware 406. Hardware 406 may include one or more hardware components that provide an operating environment for components executing in user space 402 and kernel space 404. User space 402 and kernel space 404 may represent different sections or segmentations of memory, where kernel space 404 provides higher privileges to processes and threads than user space 402. For instance, kernel space 404 may include operating system 420, which operates with higher privileges than components executing in user space 402.

As shown in FIG. 4, hardware 406 includes one or more processors 408, input components 410, storage components 412, communication units 414, and output components 416. Processors 408, input components 410, storage components 412, communication units 414, and output components 416 may each be interconnected by one or more communication channels 418. Communication channels 418 may interconnect each of the components 408, 410, 412, 414, and 416 for inter-component communications (physically, communicatively, and/or operatively). In some examples, communication channels 418 may include a hardware bus, a network connection, one or more inter-process communication data structures, or any other components for communicating data between hardware and/or software.

One or more processors 408 may implement functionality and/or execute instructions within server device 114A. For example, processors 408 on server device 114A may receive and execute instructions stored by storage components 412 that provide the functionality of components included in kernel space 404 and user space 402. These instructions executed by processors 408 may cause server device 114A to store and/or modify information, within storage components 412 during program execution. Processors 408 may execute instructions of components in kernel space 404 and user space 402 to perform one or more operations in accordance with techniques of this disclosure. That is, components included in user space 402 and kernel space 404 may be operable by processors 408 to perform various functions described herein.

One or more input components 410 of server device 114A may receive input. Examples of input are tactile, audio, kinetic, and optical input, to name only a few examples. Input components 410 of server device 114A, in one example, include a mouse, keyboard, voice responsive system, video camera, buttons, control pad, microphone or any other type of device for detecting input from a human or machine. In some examples, input component 410 may be a presence-sensitive input component, which may include a presence-sensitive screen, touch-sensitive screen, etc.

One or more output components 416 of server device 114A may generate output. Examples of output are tactile, audio, and video output. Output components 416 of server device 114A, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output.

Output components 416 may be integrated with server device 114A in some examples. In other examples, output components 416 may be physically external to and separate from server device 114A, but may be operably coupled to server device 114A via wired or wireless communication. An output component may be a built-in component of server device 114A located within and physically connected to the external packaging of server device 114A (e.g., a screen on a mobile phone). In another example, an output component, such as a presence-sensitive screen, may be an external component of server device 114A located outside and physically separated from the packaging of server device 114A (e.g., a monitor, a projector, etc. that shares a wired and/or wireless data path with a tablet computer). Output components 416 may provide haptic, vibratory or other tactile output.

One or more communication units 414 of server device 114A may communicate with external devices by transmitting and/or receiving data. For example, server device 114A may use communication units 414 to transmit and/or receive radio signals on a radio network such as a cellular radio network. Examples of communication units 414 include a network interface card (e.g. such as an Ethernet card), an optical transceiver, a radio frequency transceiver, or any other type of device that can send and/or receive information. Other examples of communication units 414 may include Bluetooth®, 3G, 4G, and Wi-Fi® radios found in mobile devices as well as Universal Serial Bus (USB) controllers and the like.

One or more storage components 412 within server device 114A may store information for processing during operation of server device 114A. In some examples, storage device 412 is a temporary memory, meaning that a primary purpose of storage device 412 is not long-term storage. Storage components 412 on server device 114A may configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage components 412, in some examples, also include one or more computer-readable storage media. Storage components 412 may be configured to store larger amounts of information than volatile memory. Storage components 412 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage components 412 may store program instructions and/or data associated with components included in user space 402 and/or kernel space 404.

As shown in FIG. 4, application 428 executes in user space 402 of server device 114A. Application 428 may be logically divided into presentation layer 422, application layer 424, and data layer 426. Presentation layer 422 may include user interface (UI) component 425, which generates and renders user interfaces of application 428. Application layer 424 may include location management component (LMC) 427, rule enforcement component (REC) 429, and notification component 430.

Data layer 426 may include one or more data stores. A data store may store data in structure or unstructured form. Example data stores may be any one or more of a relational database management system, online analytical processing database, table, or any other suitable structure for storing data. Monitored person data 434 may include information descriptive of monitored persons and/or monitoring users. Example data, may include unique identifier for monitored person or user, name, address, phone number, notes, or any other descriptive information of a monitored person or monitored person, such as a type of offense, a degree of offense (e.g., a legal degree of offense, such as second degree battery), or the like.

Location data 436 may include GNSS locations of BWTDs and other data associated with the GNSS locations. For instance, a record or other instance of location data in location data 436 may include, but is not limited to, any one or more of: unique identifier of BWTD and/or monitored person wearing BWTD, timestamp, GNSS coordinates (latitude, longitude), GNSS signal strength, signal strength of cellular tower, and directional heading of BWTD, speed at which a BWTD is traveling, whether a BWTD is at rest, an ambient temperature in which a BWTD is located, whether a BWTD is in motion without a GNSS signal, or the like. The data included in a record or other instance of location data in location data 436 may be a tuple or set of data sent by a BWTD to monitoring center 112, as described in FIG. 1.

Data layer 426 also includes monitoring rules data 438. Monitoring rules data 438 may include condition-action rules as described elsewhere in this disclosure. The condition-action rules may be based on various types of data such as, one or more of: a restricted area, a permissible area, a time period for permitted travel with respect to a restricted/permissible area, permissible/restricted users who can or cannot be within a threshold distance of the monitored person, grace periods, or any other property, rule, condition, to name only a few examples. In some examples, monitoring rules 438 defines a permissible bounded area that one or more monitored persons are permitted to travel when the BWTD assigned to the respective monitored person is unable to determine its current GNSS coordinates. For example, monitoring rules 438 may include, for one or more monitored persons, a rule having a condition specifying a respective threshold distance that the monitored person is permitted to travel when the BWTD assigned to that monitored person is unable to determine its current GNSS coordinates. As another example, monitoring rules 438 may include, for one or more monitored persons, a rule having a condition based on a set of GNSS coordinates that form a bounded area in which the respective monitored person is permitted to travel. Thus, in some examples, monitoring rules 438 may specify conditions based on one or more bounded areas that are customized to the respective monitored persons. In some instances, the monitoring rules defined by monitoring rules data 438 may be established based on conditions of release or parole of a monitored person. However, the monitoring rules need not be court mandated.

In operation, BWTD 106 may be attached and assigned to monitored target 104. LMC 427 may receive a unique identifier of BWTD 106 and/or a unique identifier of monitored target 104. LMC 427 may store data defining an association between the unique identifier of BWTD 106 and the unique identifier of monitored target 104. As monitored target 104 moves within one or more different geographic regions, LMC 427 may receive location data from BWTD 106 including, but not limited to: a unique identifier of BWTD 106 and/or monitored person wearing BWTD 106, GNSS coordinates (latitude, longitude), a timestamp when the GNSS coordinates (latitude, longitude) were determined, GNSS signal strength when the GNSS coordinates (latitude, longitude) were determined, signal strength of a tower when the GNSS coordinates (latitude, longitude) were determined, and/or a directional heading of BWTD 106 when the GNSS coordinates (latitude, longitude) were determined. In some scenarios, location data 436 may also include a timestamp when GNSS coordinates of BWTD 106 were not able to be determined and the last known location of BWTD 106. In these scenarios, location data may also include motion data generated by one or more sensor components 344 of FIG. 3, and/or a net distance and net direction from the last known location of BWTD 106. LMC 427 may store such location data within location data 436.

REC 429 may determine whether any other property, rule, condition of monitoring rules data 438 is satisfied, and which may include data that defines, one or more of: activity-dependent rules, a restricted area, a permissible area, a time period for permitted travel with respect to a restricted/permissible area, permissible/restricted users who can or cannot be within a threshold distance of the monitored person, or any other property, rule, condition. For instance, REC 429 may determine whether any other property, rule, condition is satisfied based on receiving one or more of GNSS locations from LMC 427, location data 436, and monitoring rules data 438.

While BWTD 106 is described in FIGS. 1-3 as determining whether conditions of various condition-action rules have been satisfied, in some examples, server device 114A determines whether conditions of the condition-action rules have been satisfied. For example, REC 429 of server device 114A may determine that a condition of a condition-action rule has been satisfied when a grace period has expired or when a net distance traveled by BWTD 106 is greater than a threshold. Responsive to determining that a condition of an activity-dependent rule is satisfied, REC 429 may perform an action, such as causing notification component 430 to generate an alert.

Notification component 430 generate alerts. In some examples, an alert indicates that monitoring target is potentially at an unauthorized location. For example, notification component 430 may send notifications (or messages) to computing devices external to server device 114A that cause such computing devices to output alerts, which may be visual, audio, haptic or any other type of discernable feedback. In this way, violations, statuses, or any other information may be communicated to devices of monitored persons and monitoring users. In some examples, events that cause notifications or messages to be sent by notification component 430 may also be logged by LMC 427, REC 429, and/or notification component 430 in monitored person data 434.

In some examples, UI component 425 acts as an intermediary between various components and modules of server device 114A to process and send input detected by input devices to other components and modules, and generate output from other components and modules that may be presented at one or more output devices. For instance, UI component 425 may generate one or more user interfaces for display, which may include data and/or graphical representations of maps, alerts, reports, or other communications as described in this disclosure.

According to aspects of this disclosure, application layer 424 includes rule adjustment component 432. In general, rule adjustment component 432 may enable server device 114A to adjust condition-action rules. For instance, rule adjustment component 432 may enable server device 114A to adjust a boundary of an area that the monitored target 104 assigned to wear BWTD 106 is permitted to traverse when BWTD 106 is unable to determine its GNSS coordinates. The updated boundary may correspond to only the first location (e.g., a monitored person's place of employment) or may be a global boundary for all locations (e.g., the location of the monitored person whenever the BWTD loses a GNSS signal).

In accordance with some examples of this disclosure, REC 429 may receive data generated by sensors of BWTD 106. REC 429 may determine an activity of monitored target 104 based on the data generated by the sensors. REC 429 may use various techniques known in the art for determining the activity of the user based on the data generated by the sensors. Additionally, in some examples, REC 429 may determine, based on the data generated by the sensors, a distance traveled by BWTD 106. REC 429 may use the techniques described above with respect to rule processing component 315 (FIG. 3) to determine the distance traveled by BWTD 106.

Figure 5:
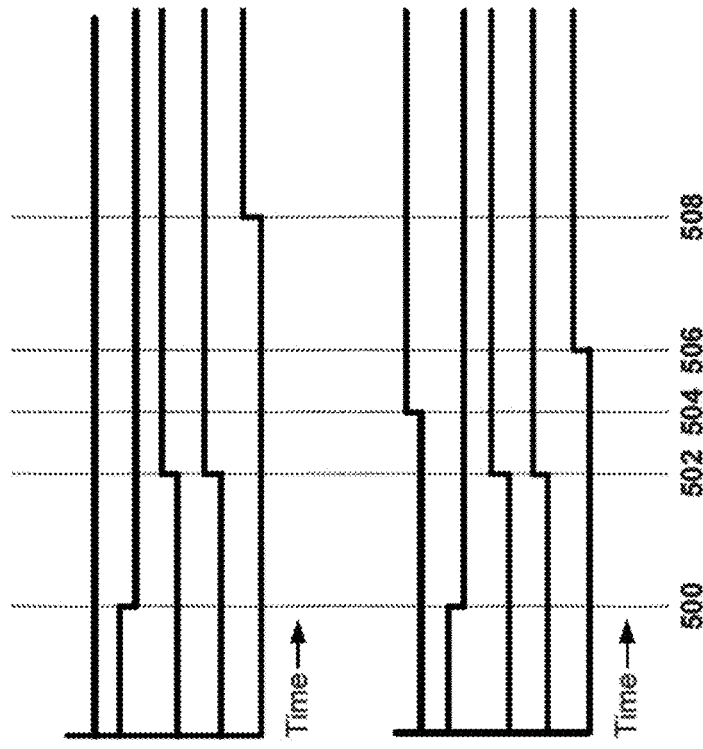
FIG. 5A is an example signal diagram in which a monitoring system does not use an activity-based rule for car motion.
FIG. 5B is an example signal diagram in which a monitoring system uses an activity-based rule for car motion, in accordance with one or more aspects of this disclosure.

FIG. 5A is an example signal diagram in which monitoring system 100 does not use an activity-based rule for car motion. FIG. 5B is an example signal diagram in which monitoring system 100 uses an activity-based rule for car motion, in accordance with one or more aspects of this disclosure. In FIG. 5A and FIG. 5B, each line indicates whether a signal is active or inactive.

A BWTD of FIG. 5A and a BWTD of FIG. 5B may both lose a GNSS signal at time 500 and may both determine that GNSS connectivity has been lost at time 502. Since the BWTD of FIG. 5A does not determine an activity of a wearer of the BWTD, the BWTD of FIG. 5A does not detect an acceleration at time 504 consistent with car motion. Hence, in FIG. 5A, the "acceleration is detected" signal is always inactive. Because the BWTD of FIG. 5A has lost GNSS connectivity, the BWTD of FIG. 5A starts a grace period which expires at time 508.

In contrast, the BWTD of FIG. 5B determines the activity of a wearer of the BWTD and hence detects, at time 504, an acceleration consistent with car motion. In the example of FIG. 5B, an activity-dependent rule for car motion specifies that the BWTD must regain GNSS connectivity prior to the expiration of a grace period shorter than the grace period used in FIG. 5A. Hence, if the BWTD of FIG. 5B does not regain GNSS connectivity by time 506, the wearer of the BWTD of FIG. 5B may be in violation. Note that time 506 is earlier than time 508. This shorter grace period may be desirable because the wearer is engaged in an activity deemed dangerous. In another example, an activity-dependent rule for sleeping may provide a grace period that expires after time 508.

Figure 6:
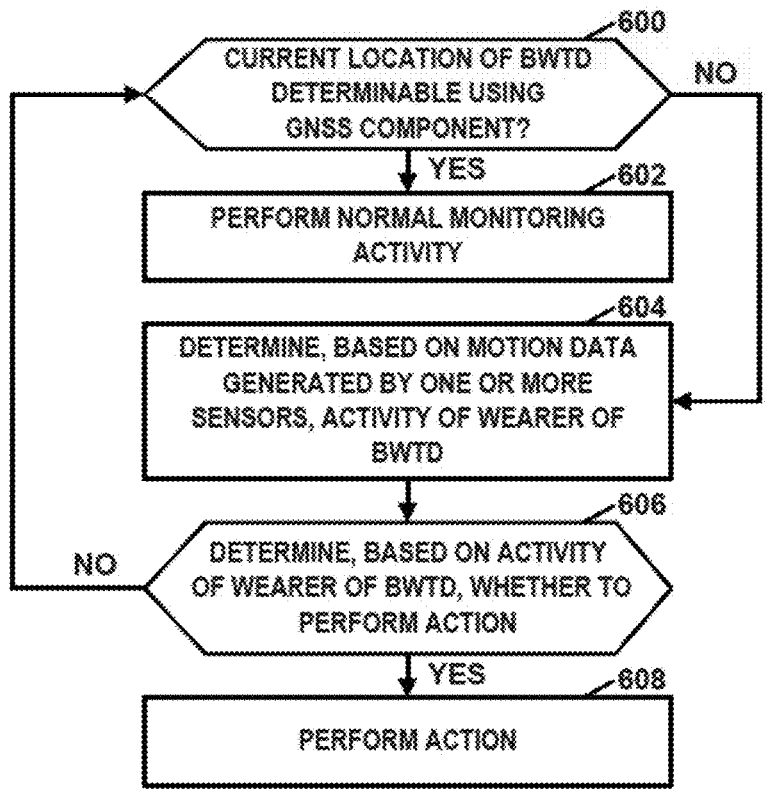
FIG. 6 is a flow diagram illustrating an example operation of a monitoring system, in accordance with aspects of this disclosure.

FIG. 6 is a flow diagram illustrating an example operation of monitoring system 100, in accordance with one or more aspects of this disclosure. While described with respect to monitoring system 100 of FIG. 1, it should be understood that the process described with respect to FIG. 6 may be carried out by a variety of other systems.

In the example of FIG. 6, BWTD 106 determines whether a current location of BWTD 106 can be determined using GNSS components 343 (FIG. 3) of BWTD 106 (600). For example, GNSS components 343 of BWTD 106 may receive GNSS signals from a threshold number (e.g., three or more) GNSS satellites 108 and may determine GNSS coordinates of BWTD 106 based on the received GNSS signals according to algorithms well-known in the art. Each signal received from a respective satellite 108 includes data such as the location of the respective satellite 108 and the time at which the data was sent by the respective satellite. BWTD 106 may use trilateration to determine the location of BWTD 106 based on the data in the received GNSS signals. In some examples, BWTD 106 is unable to determine the current location of BWTD 106 using GNSS components 343 when GNSS components 343 receiving GNSS signals from fewer than the threshold number of satellites 108 such that BWTD 106 is unable to determine the current location of BWTD 106 using the GNSS components 343.

Responsive to determining the current location of BWTD 106 using GNSS components 343 ("YES" branch of 600), monitoring system 100 may continue performing normal monitoring activity (602). For instance, BWTD 106 may again determine whether the current location of BWTD 106 can be determined using GNSS components 343. Furthermore, in some examples, BWTD 106 stores GNSS coordinates and timestamps for sets of GNSS coordinates. In some examples, BWTD 106 sends a unique identifier for BWTD 106, GNSS coordinates, a timestamp, and/or other information to monitoring center 112 (FIG. 1), where the unique identifier, GNSS coordinates, and timestamp may be stored by one or more of server devices 114 (FIG. 1). In normal monitoring activity, monitoring system 100 (e.g., monitoring center 112, user device 116) may generate an alert if the GNSS coordinates sent by BWTD 106 indicate that BWTD 106 is not in an authorized location.

Furthermore, in the example of FIG. 6, responsive to determining that the current location of BWTD 106 cannot be determined using GNSS components 343 ("NO" branch of 600), monitoring system 100 may determine, based on data generated by one or more sensors (e.g., sensor components 344 (FIG. 3)), an activity of a wearer of BWTD 106 (604). The activity of the wearer may be a form of locomotion or a sedentary activity. Monitoring system 100 may determine the activity of the wearer of BWTD 106 in various ways. An example technique for determining the activity of the wearer is described elsewhere in this disclosure with respect to FIG. 7 through FIG. 9. In some examples, monitoring system 100 determines the activity of the wearer of the BWTD based on data generated by the accelerometer, data generated by the gyroscope, and data generated by the magnetometer. In some examples, BWTD 106 determines the activity of the wearer. In some examples, one or more of server devices 114 receive sensor data and use the sensor data to determine the activity of the wearer of BWTD 106.

In other examples, monitoring system 100 does not wait to determine the activity of the wearer of BWTD 106 until after determining that BWTD 106 has lost GNSS connectivity. For instance, monitoring system 100 may determine the current activity of the wearer of BWTD 106 on a periodic basis regardless of whether BWTD 106 has GNSS connectivity.

Furthermore, in the example of FIG. 6, monitoring system 100 may determine, based on the activity of the wearer of BWTD 106 and based on a determination that the current location of BWTD 106 cannot be determined using the GNSS component, whether to perform an action (606). In other words, monitoring system 100 may calculate compliance for the activity of the wearer. For example, monitoring system 100 may be configured with a set of condition-action rules. Monitoring system 100 may make the determination to perform the action based on a condition of a condition-action rule being satisfied. The condition-action-rule may specify the action. The condition-action rules may include one or more activity-dependent rules. As described elsewhere in this disclosure, one of the conditions of an activity dependent rule is that the wearer of BWTD 106 is performing a particular activity. For instance, each respective activity-dependent rule in a set of activity-dependent rules may specify a condition that is satisfied if the wearer of BWTD 106 performs a particular activity of a plurality of activities and if the current location of BWTD 106 is not determinable using the GNSS component. There may be different activities for each activity, each there may be a different compliance calculation for each activity (e.g., walking, driving, etc.). In some examples, the action/compliance calculation determines whether an offender is in violation of parole.

In some examples, BWTD 106 evaluates the condition-action rules. In other examples, a device in monitoring system 100 other than BWTD 106 evaluates the condition-action rules. For instance, one or more server devices 114 may evaluate the condition-action rules. In one example, the device may receive from BWTD 106 an indication of the activity of the wearer of BWTD 106 or determine, based on data generated by sensor components 344 of BWTD 106, the activity of the wearer of BWTD 106. In this example, the device may evaluate the condition-action rules based on the activity of the wearer of BWTD 106.

Responsive to a determination not to perform the action ("NO" branch of 606), BWTD 106 may again determine whether the current location of BWTD 106 is determinable using GNSS components 343 (600). In other words, BWTD 106 may determine again whether BWTD 106 has GNSS connectivity. However, responsive to a determination to perform the action ("YES" branch of 606), monitoring system 100 may perform the action (608). The action may be specified by a condition-action rule whose condition is determined to be satisfied in action (606). In some examples, as part of performing the action, monitoring system 100 generates an alert. Thus, since different activities may be associated with different actions, alerts may be tuned to specified detected activities. The alert may comprise an indication that BWTD 106 is potentially at an unauthorized location. In some examples, performing the action comprises sending a message to user device 116 of monitoring user 118. Various devices in monitoring system 100 may output the alert. For example, BWTD 106 may send a message to another computing device (e.g., server devices 114 of monitoring center 112, or to a mobile device associated with the monitored target 104 assigned to wear BWTD 106) indicating BWTD 106 is potentially at an unauthorized location. The unauthorized location may be any location at which the wearer of BWTD 106 is not authorized to be. As another example, BWTD 106 may output a notification (e.g., audible, visual, or tactile) indicating that BWTD 106 is potentially at an unauthorized location. In some examples, BWTD 106 may output a notification instructing the wearer to move to a GNSS-accessible location. For instance, BWTD 106 may vibrate, which may indicate to monitored target 104 that he or she should return to an authorized location or proceed to an area where BWTD 106 is able to determine the current location of BWTD 106 using GNSS components 343.

In other examples, a device of monitoring system 100 other than BWTD 106 generates the alert. For example, server devices 114 may generate the alert. In another example, BWTD 106 may send, and server devices 114 may receive, data indicating that the selected rule has been violated. In this example, in response to receiving the data indicating that the selected rule has been violated, server devices 114 may generate the alert.

As noted elsewhere in this disclosure, various devices and components in monitoring system may perform various actions. For example, BWTD 106 may include the GNSS component, one or more sensors, and BWTD 106 may include one or more processors in the set of processors. In this example, one or more processors in BWTD 106 to perform at least one of: determining that the current location of BWTD 106 cannot be determined using the GNSS component; determining, based on the data generated by the one or more sensors, the activity of the wearer of BWTD 106; determining, based in part on the activity of the wearer of BWTD 106 and based on the determination that the current location of BWTD 106 cannot be determined using the GNSS component, whether to perform the action; and performing the action in response to the determination to perform the action. In another example, a server device remote from BWTD 106 (e.g., server device 110A) may include one or more processors in the set of processors. Instructions may cause the one or more processors in the server device to perform at least one of: determining that the current location of BWTD 106 cannot be determined using the GNSS component; determining, based on the data generated by the one or more sensors, the activity of the wearer of BWTD 106; determining, based in part on the activity of the wearer of BWTD 106 and based on the determination that the current location of BWTD 106 cannot be determined using the GNSS component, whether to perform the action; and performing the action in response to the determination to perform the action.

Figure 7:
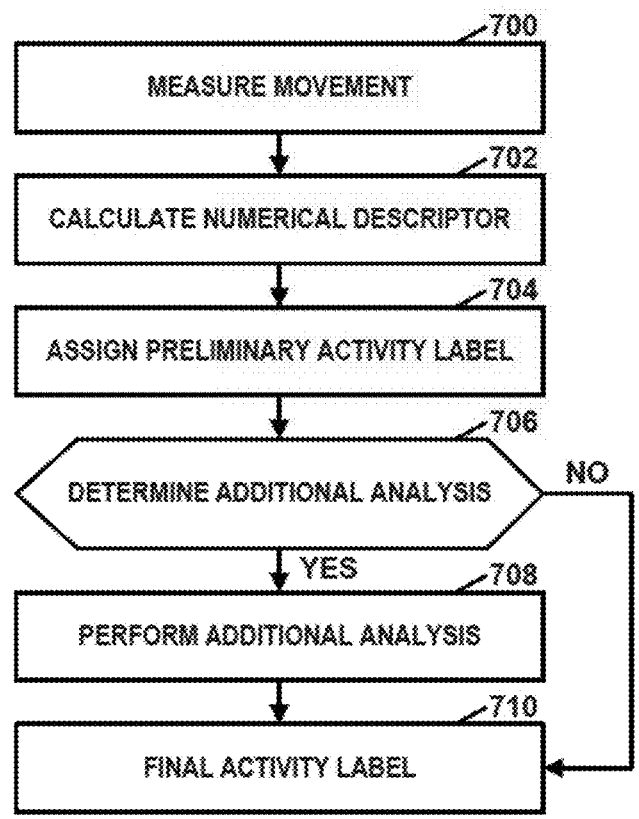
FIG. 7 is a flow diagram illustrating an example operation of a body-worn tracking device (BWTD) to determine an activity, in accordance with one or more aspects of this disclosure.

FIG. 7 is a flow diagram illustrating an example operation of a body-worn tracking device (BWTD) to determine an activity, in accordance with one or more aspects of this disclosure. In step (700), a movement sensor (e.g., accelerometer components 346) measures the movement of a person wearing BWTD 106. When BWTD 106 measures the movement of the person, the data associated with that measurement may be in a variety of forms or units, and may depend on the type of movement sensor included in BWTD 106. As an example, if an accelerometer is used as a sensor, measurement may be quantified in meters per second per second (m/s2) or g-force (g). A gyroscope may quantify data as torque measured in Newton meters (N·m). The data collected to measure movement can be collected at any desired sample rate. In some instances, the sample rate may be in the range of one (1) Hz to twenty (20) Hz. Sampling occurs over a series of time windows such that there are multiple samples taken per time window. An exemplary time window may be in the range of 1 to 10 seconds, more specifically, in the range of 4 to 8 seconds, and for example, an exemplary time window may last for 6 seconds.

In step (702), BWTD 106 calculates at least one numerical descriptor associated with the data sampled over one or more time windows. The numerical descriptor is a number computed based on the data sampled from a signal measured by the movement sensor. The numerical descriptor may be based on a single measured signal or on multiple measured signals. For example, when the movement sensor detects inertial movement along three axes, the numerical descriptor may be calculated based on the data associated with each of the three axes. The numerical descriptor may be determined for each data point related to the measured signal(s) or may be based on a lower sampling rate than the data from the measured signals. In some instances, two or more numerical descriptors may be associated with each time window.

In step (704), BWTD 106 assigns a preliminary activity label to each time window. In some instances, BWTD 106 assigns more than one preliminary activity label to a given time window. The preliminary activity label may be based on the use of the measured signal or the numerical descriptor. For example, BWTD 106 may use a decision tree to determine a preliminary activity for a given time window. Depending on the value of the data from the measured signal and the numerical descriptor, the confidence indicator associated with the assignment of a given preliminary activity label to a given time window may vary. A confidence indicator may be a scalar number, a probability, or some other method of designating confidence of the accuracy of the given preliminary activity label. In instances where more than one preliminary activity labels is assigned to a time window, each preliminary activity label may also have a confidence indicator associated with it. Examples of preliminary activity labels include: walking, driving, sleeping, sitting, running, eating, and bicycling. Other preliminary activity labels may also be assigned depending on the importance of identifying various activities.

In step (706), BWTD 106 determines whether additional analysis is to be performed prior to assigning a final activity label in step (710). The determination of whether to perform the additional analysis may depend on a variety of factors. In one configuration, it may be dependent on the confidence indicator associated with the particular time window. For example, if a confidence indicator is indicated as a probability, the confidence indicator having a value below a predefined threshold probability may require additional analysis prior to assigning a final activity label. In instances where BWTD 106 assigns more than one preliminary activity label, with each preliminary activity label having a confidence indicator within a predefined margin of each other, BWTD 106 may then determine to perform additional analysis. In such a configuration, BWTD 106 may adjust the predefined margin over time.

In other configurations, BWTD 106 may determine whether to perform additional analysis when the preliminary activity label is a commonly confused preliminary activity. Examples of commonly confused activities may be slow moving, low energy activities such as sitting compared to driving or fast moving, high energy activities like running compared against bicycling. In other instances, the current device status may be a factor for determining whether to perform additional analysis. For example, if the activity recognition device has a "low battery" state, this factor may weigh in favor of performing additional analysis prior to assigning a final activity label to a time window. Additionally, a low battery status may be a condition for the current device to send data to an exterior or external processor for additional processing prior to determining a final activity label.

If BWTD 106 determines that no additional analysis should be performed ("NO" branch of 706), BWTD 106 assigns a final activity label to the time window as shown in step (710). However, if BWTD 106 determines that additional analysis should be performed ("YES" branch of 706), the activity recognition proceeds to step (708) to perform additional analysis.

In step (708), where BWTD 106 determines that additional analysis should be performed, the analysis may be performed locally on BWTD 106, or may be performed remotely by an external processor, such as some type of central monitoring system including, but not limited, computation in a cloud environment. Additional analysis may include computational escalation, such as performing more complex or resource intensive computations than were performed for the purpose of determining a preliminary activity label. Additional analysis may include at least one of the following algorithm techniques: neural networks, Bayesian analysis, random forest, support vector machine, and multi-level decision tree.

In step (710), BWTD 106 assigns a final activity label to the time window. In some instances, BWTD 106 has not have performed additional analysis and the final activity label is the same as the preliminary activity label. In other instances, BWTD 106 assigns the final activity label to the time window based on the preliminary activity label for the time window and at least one final activity label for at least one prior time window. In some instances, BWTD 106 may transmit an alarm signal to a central monitoring system (e.g., monitoring system 112) upon determination of a particular final activity label.

Figure 8:
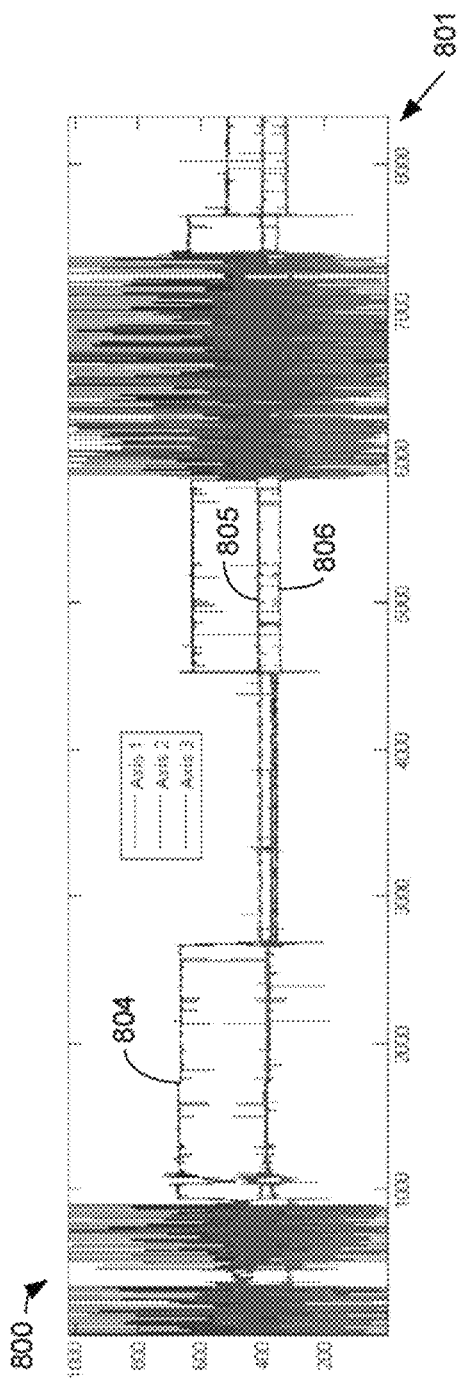
FIG. 8 is an accelerometer data graph showing exemplary data of a BWTD worn by an individual over a period of approximately 384 seconds.

FIG. 8 is an accelerometer data graph 50 showing exemplary data of BWTD 106 worn by an individual over a period of approximately 384 seconds. Graph 800 shows the magnitude of three axes 804, 805 and 806 of movement as measured by an accelerometer, across a time axis 801. Data axis 84, 805, 806 includes both a static component (driven by gravity) and a dynamic component. The sample rate for this particular graph was 20 Hz, the sampling period extends over 384 seconds.

Figure 9:
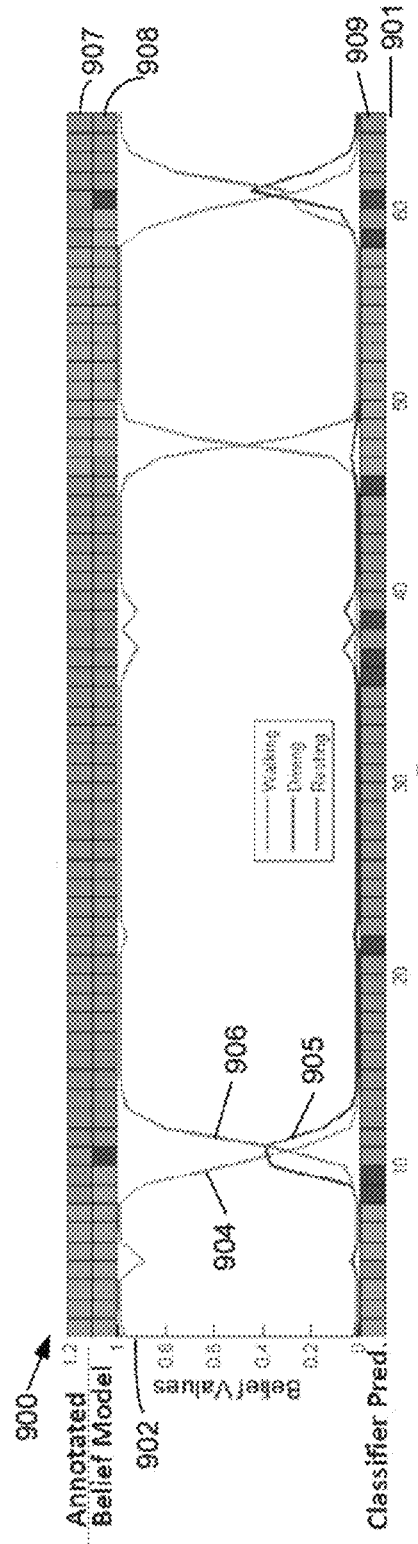
FIG. 9 shows a graph illustrating example belief values for activity labels associated with the movement data from FIG. 8 over multiple time windows.

FIG. 9 shows graph 900 illustrating belief values for activity labels associated with the movement data from FIG. 8 over multiple time windows. The horizontal axis 901 shows time over 6-second time windows. Shorter or longer time windows could be used consistent with the present disclosure. The vertical axis 902 shows belief values related to each of the activities, walking 904, driving 905 or resting 906, during a given time window. Belief values can be associated with a likelihood that a given activity is being performed during a given time window. Belief values differ from confidence indicators in that the sum of all belief values for all activities for a particular time window is 1.0.

The top layer of activity labels indicates the actual activity labels 907 for the activity being performed by the person wearing the activity monitoring device as recorded by that individual. During approximately the first seven time windows, the individual was walking. During time windows 8-45, the individual was resting. From time windows 45 to 57, the individual was walking again. And during time windows 58-64, the individual was resting.

The bottom layer of activity labels indicates preliminary activity labels 909 for each time window based on the accelerometer data associated with that time window as shown in FIG. 8. There are more frequent transitions between activities as shown in the preliminary activity labels 909 than when compared to actual activity labels 907.

Final activity labels 908, shown directly below actual activity labels 907 show changes made to the preliminary activity labels 909 after additional analysis. The additional analysis was based in part on the confidence indicator for the assigned activity during a given time window. As can be seen, the final activity labels 908 have a high degree of accuracy when compared with actual activity labels 907. Confidence indicators for walking 904, driving 905 and resting 906 are not shown in FIG. 9. However, a confidence indicator for the preliminary activity label for each time window could be calculated the belief values.

For example, in FIG. 9, the belief value for each activity is represented by the lines 904, 905, 906. As the actual activity label 907 changes, the associated belief values change. A confidence indicator for the preliminary activity label 909 could be derived by looking at how close the belief values are to one another. For example, during time window 11, all three belief values are close to one another, i.e. all roughly around 0.33. During this time window, a calculated confidence indicator would be very low because the belief values indicate that all activities have an equal chance of being the actual activity of the user. In this case, the device may send data related to time window 11 to a remote processor for escalated or additional processing.

Figure 10:
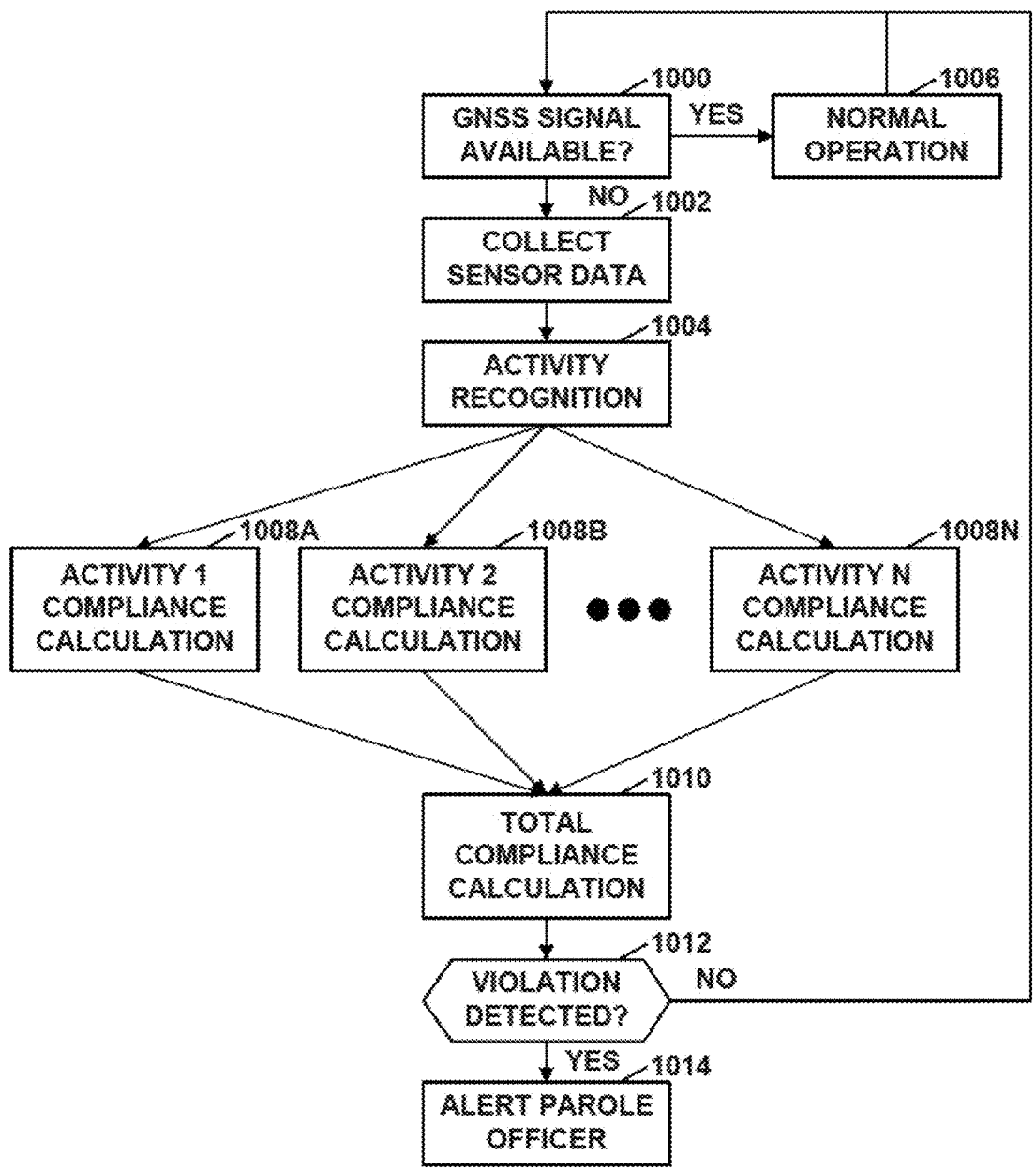
FIG. 10 is a flowchart illustrating an example operation of this disclosure, in accordance with one or more aspects of this disclosure.

FIG. 10 is a flowchart illustrating an example operation of this disclosure, in accordance with one or more aspects of this disclosure. In the example of FIG. 10, when the GNSS signal is not available to BWTD 106 ("NO" branch of 1000), sensor data is collected (1002) and used to recognize an activity (1004). If the GNSS signal is available to BWTD 106 ("YES" branch of 1000), normal operation of monitoring system 100 continues (1006). After activity recognition when the GNSS signal is not available to BWTD 106, monitoring system 100 may calculate compliance specifically for the type of activity detected (e.g., performs one or more of activities 1008A-1008N). For example, monitoring system 100 may evaluate a condition of a condition-action rule for the determined activity. Thus, in the example of FIG. 10, there may be a different compliance calculation for each activity (e.g., walking, driving, etc.). Monitoring system 100 calculates a total compliance for the period in which BWTD 106 has lost the GNSS signal (1010). In the example of FIG. 10, the compliance calculation determines whether or not the offender is in violation of parole. During this compliance calculation step, monitoring system 100 can adaptively adjust whether to alert a parole officer (1014). This alert is timed to the specific activity that was detected. Thus, the ability to differentiate activities of the offender using accelerometer data enables us to be able to adaptively adjust the time until we alert the parole officer.

Figure 11:
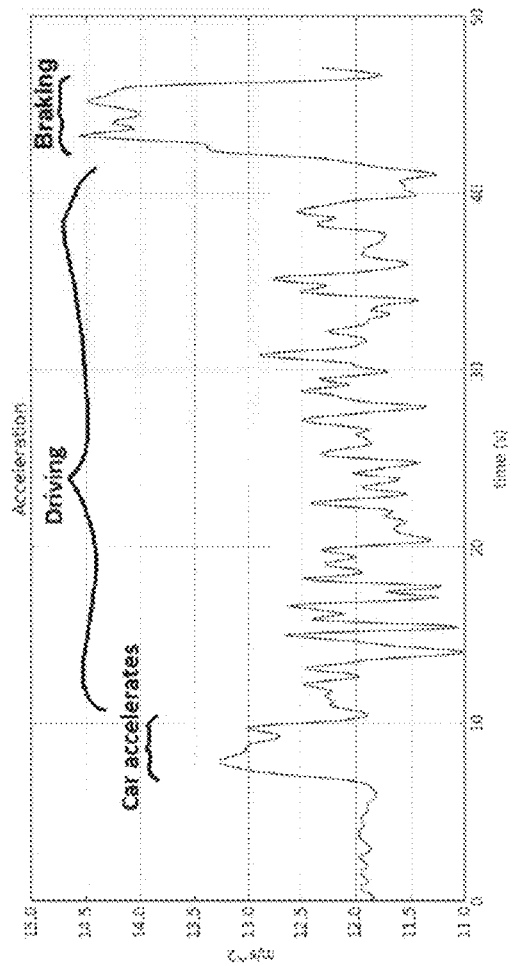
FIG. 11 is an example chart illustrating acceleration data captured while driving a car.

FIG. 11 is an example chart illustrating acceleration data captured while driving a car. In the example of FIG. 11, the car is already running at the start. Then the car is put into gear and accelerated to highway speed. The car is driven along a countryside highway. Braking occurs near the end. The car is parked at the end of data collection. If monitoring system 100 integrates over the "car accelerates" portion of this plot, monitoring system 100 can identify the car acceleration event.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

What is claimed is:

1. A system for tracking a location of a body-worn tracking device (BWTD), the system comprising:
 a global navigation satellite system (GNSS) component;
 one or more sensors;
 a set of one or more processors; and
 one or more memory devices comprising:
  instructions that, when executed by the one or more processors, cause the one or more processors to:
   determine whether a current location of the BWTD can be determined using the GNSS component;
   determine, based on data generated by the one or more sensors, an activity of a wearer of the BWTD, the activity of the wearer being a form of locomotion or a sedentary activity; and
   responsive to determining the activity of the wearer of the BWTD and a determination that the current location of the BWTD cannot be determined using the GNSS component, performing an action, wherein the instructions cause the one or more processors to:

(i) determine whether to perform the action based on whether a condition specified by an activity-dependent rule in a set of activity-dependent rules is satisfied, each respective activity-dependent rule in the set of activity-dependent rules specifying a condition that is satisfied if the wearer of the BWTD performs a particular activity of a plurality of activities and if the current location of the BWTD is not determinable using the GNSS component, (ii) determine a distance traveled, the distance traveled being a net distance traveled by the BWTD from a location at which the one or more processors were most recently able to determine the current location of the BWTD using the GNSS component, wherein the set of activity-dependent rules includes a first rule and a second rule, satisfaction of the first rule requiring the wearer of the BWTD to perform a first activity, the BWTD to have lost GNSS connectivity, and the distance traveled to be greater than a first threshold, satisfaction of the second rule requiring the wearer of the BWTD to perform a second activity, the BWTD to have lost GNSS connectivity, and the distance traveled to be greater than a second threshold, and the first activity being different from the second activity, and the first threshold being different from the second threshold, wherein the one or more sensors include an accelerometer and a directionality sensor, the directionality sensor comprising a gyroscope or a magnetometer, wherein instructions that cause the one or more processors to determine the net distance cause the one or more processors to:

detect, based on data generated by an accelerometer, a plurality of steps;

determine an estimated distance traveled during each step of the plurality of steps;

determine, based on the data generated by the directionality sensor, a direction of travel of each step of the plurality of steps; and determine, based on the estimated distance traveled during each step and the direction of travel of each step, the net distance between the current location of the BWTD and the location at which the one or more processors were most recently able to determine the current location of the BWTD using the GNSS component.

2. The system of claim 1, wherein the action comprises configuring the BWTD with a particular grace period that is based at least in part on the determined activity of the wearer.

3. The system of claim 1, wherein the plurality of activities includes at least one of: walking, running, driving or riding in or on a motor vehicle, bicycling, swimming, skating, and skateboarding.

4. The system of claim 1, wherein the set of activity-dependent rules includes a first rule and a second rule, satisfaction of the first rule requiring the wearer of the BWTD to perform a first activity, the BWTD to have lost GNSS connectivity, and a first grace period to have expired prior to the BWTD regaining GNSS connectivity, satisfaction of the second rule requiring the wearer of the BWTD to perform a second activity, the BWTD to have lost GNSS connectivity, and a second grace period to have expired prior to the BWTD regaining GNSS connectivity, and the first activity being different from the second activity, and the first grace period and the second grace period having different durations.

5. The system of claim 1, wherein the instructions that cause the one or more processors to perform the action comprise instructions that, when executed, cause the BWTD to output a notification instructing the wearer of the BWTD to move to a GNSS-accessible location.

6. The system of claim 1, wherein the one or more sensors comprise one or more of: an accelerometer and a directionality sensor, the directionality sensor comprising a gyroscope or a magnetometer, wherein the instructions cause the one or more processors to determine the activity of the wearer of the BWTD based on data generated by the accelerometer and data generated by the directionality sensor.

7. The system of claim 1, wherein the BWTD includes the GNSS component, the one or more sensors, and the BWTD includes one or more processors in the set of processors, the instructions causing the one or more processors in the BWTD to perform at least one of:

determining that the current location of the BWTD cannot be determined using the GNSS component;

determining, based on the data generated by the one or more sensors, the activity of the wearer of the BWTD;

determining, based in part on the activity of the wearer of the BWTD and based on the determination that the current location of the BWTD cannot be determined using the GNSS component, whether to perform the action; and performing the action in response to the determination to perform the action.

8. The system of claim 1, further comprising a server device remote from the BWTD, the server device including one or more processors in the set of processors, the instructions causing the one or more processors in the server device to perform at least one of:

determining that the current location of the BWTD cannot be determined using the GNSS component;

determining, based on the data generated by the one or more sensors, the activity of the wearer of the BWTD;

determining, based in part on the activity of the wearer of the BWTD and based on the determination that the current location of the BWTD cannot be determined using the GNSS component, whether to perform the action; and performing the action in response to the determination to perform the action.

9. The system of claim 1, wherein the activity corresponds to an identifiable output signature of the one or more sensors.

10. A method comprising:

determining, by a set of processors in a system for tracking a location of a body-worn tracking device (BWTD), that a current location of the BWTD cannot be determined using a global navigation satellite system (GNSS) component of the system, the set of processors including one or more processors;

determining, by the one or more processors, based on data generated by one or more sensors, an activity of a wearer of the BWTD, the activity of the wearer being a form of locomotion or a sedentary activity; and performing, by the one or more processors, an action based in part on the activity of the wearer of the BWTD and based on a determination that the current location of the BWTD cannot be determined using the GNSS component, determining, by the one or more processors, whether to perform the action based on whether a condition specified by an activity-dependent rule in a set of activity-dependent rules is satisfied, each respective activity-dependent rule in the set of activity-dependent rules specifying a condition that is satisfied if the wearer of the BWTD performs a particular activity of a plurality of activities and if the current location of the BWTD is not determinable using the GNSS component, determining, by the one or more processors, a distance traveled, the distance traveled being a net distance traveled by the BWTD from a location at which the one or more processors were most recently able to determine the current location of the BWTD using the GNSS component, wherein the set of activity-dependent rules includes a first rule and a second rule, satisfaction of the first rule requiring the wearer of the BWTD to perform a first activity, the BWTD to have lost GNSS connectivity, and the distance traveled to be greater than a first threshold, satisfaction of the second rule requiring the wearer of the BWTD to perform a second activity, the BWTD to have lost GNSS connectivity, and the distance traveled to be greater than a second threshold, and the first activity being different from the second activity, and the first threshold being different from the second threshold, wherein the one or more sensors include an accelerometer and a directionality sensor, the directionality sensor comprising a gyroscope or a magnetometer, and wherein determining the net distance comprises:

detecting, by the one or more processors, based on data generated by an accelerometer, a plurality of steps;

determining, by the one or more processors, an estimated distance traveled during each step of the plurality of steps;

determining, by the one or more processors, based on the data generated by the directionality sensor, a direction of travel of each step of the plurality of steps; and determining, by the one or more processors, based on the estimated distance traveled during each step and the direction of travel of each step, the net distance between the current location of the BWTD and the location at which the one or more processors were most recently able to determine the current location of the BWTD using the GNSS component.

11. The method of claim 10, wherein the action comprises configuring the BWTD with a particular grace period that is based at least in part on the determined activity of the wearer.

12. The method of claim 10,
wherein the plurality of activities includes at least one of: walking, running, driving or riding in or on a motor vehicle, bicycling, swimming, skating, and skateboarding.

13. The method of claim 10, wherein the set of activity-dependent rules includes a first rule and a second rule, satisfaction of the first rule requiring the wearer of the BWTD to perform a first activity, the BWTD to have lost GNSS connectivity, and a first grace period to have expired prior to the BWTD regaining GNSS connectivity, satisfaction of the second rule requiring the wearer of the BWTD to perform a second activity, the BWTD to have lost GNSS connectivity, and a second grace period to have expired prior to the BWTD regaining GNSS connectivity, the first activity being different from the second activity, and the first grace period and the second grace period having different durations.

14. The method of claim 10, wherein performing the action comprises outputting, by the BWTD, a notification instructing the wearer of the BWTD to move to a GNSS-accessible location and wherein the one or more sensors comprise one or more of:
an accelerometer and a directionality sensor, the directionality sensor comprising a gyroscope or a magnetometer, wherein determining the activity of the wearer of the BWTD comprises determining, by the one or more processors, the activity of the wearer of the BWTD based on data generated by the accelerometer and data generated by the directionality sensor.

15. The method of claim 10, wherein the BWTD includes the GNSS component, the one or more sensors, and the BWTD includes one or more processors in the set of processors, the one or more processors in the BWTD performing at least one of:

determining that the current location of the BWTD cannot be determined using the GNSS component;

determining, based on the data generated by the one or more sensors, the activity of the wearer of the BWTD;

determining based in part on the activity of the wearer of the BWTD and based on the determination that the current location of the BWTD cannot be determined using the GNSS component, whether to perform the action; and performing the action in response to the determination to perform the action.

16. The method of claim 10, wherein the system comprises a server device remote from the BWTD, the server device including one or more processors in the set of processors, the one or more processors in the server device performing at least one of:

determining that the current location of the BWTD cannot be determined using the GNSS component;

determining, based on the data generated by the one or more sensors, the activity of the wearer of the BWTD;

determining based in part on the activity of the wearer of the BWTD and based on the determination that the current location of the BWTD cannot be determined using the GNSS component, whether to perform the action; and performing the action in response to the determination to perform the action.

17. The method of claim 10, wherein the activity corresponds to an identifiable output signature of the one or more sensors.

18. A body-worn tracking device (BWTD) comprising:
a global navigation satellite system (GNSS) component;
one or more sensors;
a set of one or more processors; and one or more memory devices comprising instructions that, when executed by the one or more processors, cause the one or more processors to:
  determine whether a current location of the BWTD can be determined using the GNSS component;
  determine, based on data generated by the one or more sensors, an activity of a wearer of the BWTD, the activity of the wearer being a form of locomotion or a sedentary activity;
  responsive to a determination that the current location of the BWTD cannot be determined using the GNSS component, adjust, based on the activity of the wearer of the BWTD, a duration of a grace period; and
  generate a notification in response to determining the grace period has expired,
  wherein the instructions cause the one or more processors to:
    (i) determine whether to perform the action based on whether a condition specified by an activity-dependent rule in a set of activity-dependent rules is satisfied, each respective activity-dependent rule in the set of activity-dependent rules specifying a condition that is satisfied if the wearer of the BWTD performs a particular activity of a plurality of activities and if the current location of the BWTD is not determinable using the GNSS component,
    (ii) determine a distance traveled, the distance traveled being a net distance traveled by the BWTD from a location at which the one or more processors were most recently able to determine the current location of the BWTD using the GNSS component,
  wherein the set of activity-dependent rules includes a first rule and a second rule, satisfaction of the first rule requiring the wearer of the BWTD to perform a first activity, the BWTD to have lost GNSS connectivity, and the distance traveled to be greater than a first threshold, satisfaction of the second rule requiring the wearer of the BWTD to perform a second activity, the BWTD to have lost GNSS connectivity, and the distance traveled to be greater than a second threshold, and the first activity being different from the second activity, and the first threshold being different from the second threshold,
  wherein the one or more sensors include an accelerometer and a directionality sensor, the directionality sensor comprising a gyroscope or a magnetometer,
  wherein instructions that cause the one or more processors to determine the net distance cause the one or more processors to:
    detect, based on data generated by an accelerometer, a plurality of steps;
    determine an estimated distance traveled during each step of the plurality of steps;
    determine, based on the data generated by the directionality sensor, a direction of travel of each step of the plurality of steps; and
    determine, based on the estimated distance traveled during each step and the direction of travel of each step, the net distance between the current location of the BWTD and the location at which the one or more processors were most recently able to determine the current location of the BWTD using the GNSS component.

* * * * *